(12) United States Patent
Mitchell et al.

(10) Patent No.: US 10,039,748 B2
(45) Date of Patent: *Aug. 7, 2018

(54) PRMT1 INHIBITORS AND USES THEREOF

(71) Applicant: Epizyme, Inc., Cambridge, MA (US)

(72) Inventors: Lorna Helen Mitchell, Cambridge, MA (US); Gideon Shapiro, Gainesville, FL (US); Richard Chesworth, Concord, MA (US); Paula Ann Boriack-Sjodin, Lexington, MA (US); Oscar Miguel Moradei, Burlington, MA (US); Kevin Wayne Kuntz, Woburn, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/231,651

(22) Filed: Aug. 8, 2016

(65) Prior Publication Data

US 2017/0182005 A1    Jun. 29, 2017

Related U.S. Application Data

(63) Continuation of application No. 14/212,965, filed on Mar. 14, 2014, now Pat. No. 9,447,079.

(60) Provisional application No. 61/781,055, filed on Mar. 14, 2013.

(51) Int. Cl.
  *A61K 31/4155*    (2006.01)

(52) U.S. Cl.
  CPC .............................. *A61K 31/4155* (2013.01)

(58) Field of Classification Search
  CPC .................................................. A61K 31/4155
  See application file for complete search history.

(56) References Cited

U.S. PATENT DOCUMENTS

| | | | |
|---|---|---|---|
| 4,806,553 A | 2/1989 | Shiokawa et al. | |
| 5,011,849 A | 4/1991 | Gassner et al. | |
| 5,204,482 A | 4/1993 | Gassner et al. | |
| 5,932,737 A | 8/1999 | Itoh et al. | |
| 6,566,376 B1 | 5/2003 | Baxter et al. | |
| 6,914,160 B1 | 7/2005 | Armour et al. | |
| 7,485,722 B2 | 2/2009 | Egle et al. | |
| 7,629,294 B2 | 12/2009 | Gebauer et al. | |
| 7,632,855 B2 | 12/2009 | Barrilalonso et al. | |
| 7,709,487 B2 | 5/2010 | Van Emelen et al. | |
| 7,759,336 B2 | 7/2010 | Habashita et al. | |
| 8,063,071 B2 | 11/2011 | Kerns et al. | |
| 8,097,708 B2 | 1/2012 | Sugimoto et al. | |
| 8,133,904 B2 | 3/2012 | McElroy et al. | |
| 8,153,625 B2 | 4/2012 | Habashita et al. | |
| 8,338,437 B2 | 12/2012 | Wahhab et al. | |
| 8,906,900 B2 | 12/2014 | Duncan et al. | |
| 8,940,726 B2 | 1/2015 | Duncan et al. | |
| 8,952,026 B2 | 2/2015 | Mitchell et al. | |
| 8,993,555 B2 | 3/2015 | Duncan et al. | |
| 9,023,883 B2 | 5/2015 | Kuntz et al. | |
| 9,045,455 B2 | 6/2015 | Mitchell et al. | |
| 9,120,757 B2 | 9/2015 | Chesworth et al. | |
| 9,133,189 B2 | 9/2015 | Chesworth et al. | |
| 9,221,794 B2 | 12/2015 | Duncan et al. | |
| 9,266,836 B2 | 2/2016 | Duncan et al. | |
| 9,346,761 B2 | 5/2016 | Chesworth et al. | |
| 9,346,802 B2 | 5/2016 | Chesworth et al. | |
| 9,365,519 B2 | 6/2016 | Duncan et al. | |

(Continued)

FOREIGN PATENT DOCUMENTS

| | | |
|---|---|---|
| DE | 10149370 A1 | 4/2003 |
| EP | 1 571 146 A1 | 9/2005 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
U.S. Appl. No. 14/212,102, filed Mar. 14, 2014, Granted, U.S. Pat. No. 9,346,761.
U.S. Appl. No. 15/093,103, filed Apr. 7, 2016, Published, 2017-0057926.

(Continued)

*Primary Examiner* — Shawquia Jackson
(74) *Attorney, Agent, or Firm* — Wolf, Greenfield & Sacks, P.C.

(57) ABSTRACT

Described herein are compounds of Formula (I-a) and (I-b), pharmaceutically acceptable salts thereof, and pharmaceutical compositions thereof. Compounds of the present invention are useful for inhibiting PRMT1 activity. Methods of using the compounds for treating PRMT1-mediated disorders are also described.

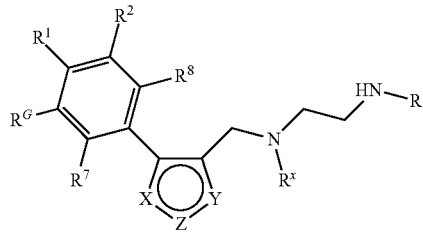

I-a

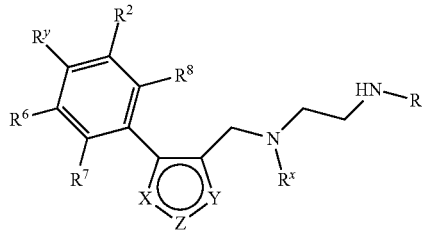

I-b

13 Claims, No Drawings

(56) References Cited

U.S. PATENT DOCUMENTS

| | | |
|---|---|---|
| 9,365,527 B2 | 6/2016 | Chesworth et al. |
| 9,365,555 B2 | 6/2016 | Duncan et al. |
| 9,388,173 B2 | 7/2016 | Duncan et al. |
| 9,394,258 B2 | 7/2016 | Chesworth et al. |
| 9,440,950 B2 | 9/2016 | Mitchell et al. |
| 9,447,079 B2 | 9/2016 | Mitchell et al. |
| 9,475,776 B2 | 10/2016 | Kuntz et al. |
| 9,598,374 B2 | 3/2017 | Chesworth et al. |
| 9,604,930 B2 | 3/2017 | Duncan et al. |
| 9,611,257 B2 | 4/2017 | Duncan et al. |
| 9,630,961 B2 | 4/2017 | Chesworth et al. |
| 9,675,614 B2 | 6/2017 | Duncan et al. |
| 9,732,041 B2 | 8/2017 | Chesworth et al. |
| 9,732,072 B2 | 8/2017 | Duncan et al. |
| 2002/0090627 A1 | 7/2002 | Meyers |
| 2004/0176325 A1 | 9/2004 | Munson et al. |
| 2005/0032794 A1 | 2/2005 | Padia et al. |
| 2005/0187224 A1 | 8/2005 | Gebauer et al. |
| 2005/0203143 A1* | 9/2005 | Breslin ............ C07D 233/64 514/326 |
| 2006/0128724 A1 | 6/2006 | Cui et al. |
| 2006/0235037 A1 | 10/2006 | Purandare et al. |
| 2006/0239990 A1 | 10/2006 | Nabel et al. |
| 2006/0264419 A1 | 11/2006 | Schiemann et al. |
| 2007/0060589 A1 | 3/2007 | Purandare et al. |
| 2008/0214615 A1 | 9/2008 | Muller et al. |
| 2008/0214654 A1 | 9/2008 | Lampe et al. |
| 2008/0280925 A1 | 11/2008 | Wahhab et al. |
| 2008/0312298 A1 | 12/2008 | Foreman et al. |
| 2009/0012031 A1 | 1/2009 | Chinnaiyan et al. |
| 2009/0036435 A1 | 2/2009 | Curry et al. |
| 2009/0143372 A1 | 6/2009 | Deng et al. |
| 2009/0298910 A1 | 12/2009 | Griffey et al. |
| 2009/0306201 A1 | 12/2009 | Reinberg et al. |
| 2010/0151506 A1 | 6/2010 | Thompson et al. |
| 2011/0003784 A1 | 1/2011 | Garvey et al. |
| 2011/0021362 A1 | 1/2011 | Trojer et al. |
| 2011/0065681 A1 | 3/2011 | Wei et al. |
| 2011/0160293 A1 | 6/2011 | Nakamura et al. |
| 2011/0251216 A1 | 10/2011 | Chinnaiyan et al. |
| 2011/0269770 A1 | 11/2011 | Gross et al. |
| 2012/0071418 A1 | 3/2012 | Copeland et al. |
| 2012/0142625 A1 | 6/2012 | Olhava et al. |
| 2012/0156219 A1 | 6/2012 | Habashita et al. |
| 2012/0264734 A1 | 10/2012 | Kuntz et al. |
| 2013/0345268 A1 | 12/2013 | Ratner et al. |
| 2014/0288105 A1 | 9/2014 | Chesworth et al. |
| 2014/0288124 A1 | 9/2014 | Chesworth et al. |
| 2014/0288128 A1 | 9/2014 | Mitchell et al. |
| 2014/0288129 A1 | 9/2014 | Mitchell et al. |
| 2014/0288140 A1 | 9/2014 | Mitchell et al. |
| 2014/0288141 A1 | 9/2014 | Kuntz et al. |
| 2014/0315904 A1 | 10/2014 | Chesworth et al. |
| 2014/0315961 A1 | 10/2014 | Chesworth et al. |
| 2014/0323537 A1 | 10/2014 | Chesworth et al. |
| 2015/0259322 A1 | 9/2015 | Kita et al. |
| 2015/0266853 A1 | 9/2015 | Kita et al. |
| 2015/0284334 A1 | 10/2015 | Kuntz et al. |
| 2015/0344433 A1 | 12/2015 | Duncan et al. |
| 2015/0344434 A1 | 12/2015 | Duncan et al. |
| 2015/0344457 A1 | 12/2015 | Duncan et al. |
| 2015/0344463 A1 | 12/2015 | Duncan et al. |
| 2015/0361042 A1 | 12/2015 | Duncan et al. |
| 2016/0024016 A1 | 1/2016 | Chesworth et al. |
| 2016/0024017 A1 | 1/2016 | Chesworth et al. |
| 2016/0031839 A1 | 2/2016 | Chesworth et al. |
| 2016/0039767 A1 | 2/2016 | Mitchell et al. |
| 2016/0039834 A1 | 2/2016 | Chesworth et al. |
| 2016/0052922 A1 | 2/2016 | Chesworth et al. |
| 2016/0108018 A1 | 4/2016 | Mitchell et al. |
| 2016/0137609 A1 | 5/2016 | Chesworth et al. |
| 2016/0137631 A1 | 5/2016 | Duncan et al. |
| 2016/0184267 A1 | 6/2016 | Chesworth et al. |
| 2016/0185772 A1 | 6/2016 | Chesworth et al. |
| 2016/0214985 A1 | 7/2016 | Duncan et al. |
| 2016/0368907 A1 | 12/2016 | Duncan et al. |
| 2017/0027935 A1 | 2/2017 | Duncan et al. |
| 2017/0056409 A1 | 3/2017 | Chesworth et al. |
| 2017/0057926 A1 | 3/2017 | Chesworth et al. |
| 2017/0088529 A1 | 3/2017 | Chesworth et al. |
| 2017/0088541 A1 | 3/2017 | Duncan et al. |
| 2017/0114061 A1 | 4/2017 | Duncan et al. |
| 2017/0119735 A1 | 5/2017 | Chesworth et al. |
| 2017/0198006 A1 | 7/2017 | Chesworth et al. |
| 2017/0210751 A1 | 7/2017 | Duncan et al. |

FOREIGN PATENT DOCUMENTS

| | | |
|---|---|---|
| EP | 2 221 053 A1 | 8/2010 |
| EP | 2 226 315 A1 | 9/2010 |
| JP | 2009-179616 A | 8/2009 |
| WO | WO 96/16981 A2 | 6/1996 |
| WO | WO 2003/031435 A1 | 4/2003 |
| WO | WO 2004/020414 A1 | 3/2004 |
| WO | WO 2004/052862 A1 | 6/2004 |
| WO | WO 2004/089931 A1 | 10/2004 |
| WO | WO 2004/096212 A1 | 11/2004 |
| WO | WO 2006/025832 A1 | 3/2006 |
| WO | WO 2006/033995 A2 | 3/2006 |
| WO | WO 2006/040136 A1 | 4/2006 |
| WO | WO 2006/069155 A2 | 6/2006 |
| WO | WO 2007/091393 A1 | 8/2007 |
| WO | WO 2008/001076 A1 | 1/2008 |
| WO | WO 2008/008286 A2 | 1/2008 |
| WO | WO 2008/104077 A1 | 9/2008 |
| WO | WO 2008/137834 A2 | 11/2008 |
| WO | WO 2009/033125 A1 | 3/2009 |
| WO | WO 2009/126537 A1 | 10/2009 |
| WO | WO 2010/034737 A1 | 4/2010 |
| WO | WO 2010/094009 A2 | 8/2010 |
| WO | WO 2010/094609 A1 | 8/2010 |
| WO | WO 2011/079236 A1 | 6/2011 |
| WO | WO 2011/082098 A1 | 7/2011 |
| WO | WO 2011/096210 A1 | 8/2011 |
| WO | WO 2011/096211 A1 | 8/2011 |
| WO | WO 2011/140324 A1 | 11/2011 |
| WO | WO 2012/005805 A1 | 1/2012 |
| WO | WO 2012/060760 A1 | 5/2012 |
| WO | WO 2012/068589 A2 | 5/2012 |
| WO | WO 2012/075080 A1 | 6/2012 |
| WO | WO 2012/075492 A2 | 6/2012 |
| WO | WO 2012/075500 A2 | 6/2012 |
| WO | WO 2012/082436 A2 | 6/2012 |
| WO | WO 2012/118812 A2 | 9/2012 |
| WO | WO 2012/142513 A1 | 10/2012 |
| WO | WO 2013/174947 A1 | 11/2013 |
| WO | WO 2014/034750 A1 | 3/2014 |
| WO | WO 2014/144659 A1 | 9/2014 |
| WO | WO 2014/153090 A1 | 9/2014 |
| WO | WO 2014/153100 A2 | 9/2014 |
| WO | WO 2014/153172 A1 | 9/2014 |
| WO | WO 2014/153208 A1 | 9/2014 |
| WO | WO 2014/153214 A1 | 9/2014 |
| WO | WO 2014/153226 A1 | 9/2014 |
| WO | WO 2014/153235 A2 | 9/2014 |
| WO | WO 2014/178954 A1 | 11/2014 |
| WO | WO 2016/044556 A2 | 3/2016 |
| WO | WO 2016/044576 A1 | 3/2016 |
| WO | WO 2016/044585 A1 | 3/2016 |
| WO | WO 2016/044626 A1 | 3/2016 |

OTHER PUBLICATIONS

U.S. Appl. No. 14/212,142, filed Mar. 14, 2014, Granted, U.S. Pat. No. 9,045,455.

U.S. Appl. No. 14/808,270, filed Jul. 24, 2015, Published, 2016-0185772.

PCT/US2014/029009, May 28, 2014, International Search Report and Written Opinion.

PCT/US2014/029160, May 28, 2014, International Search Report and Written Opinion.

PCT/US2014/029583, Jul. 29, 2014, International Search Report and Written Opinion.

(56) References Cited

OTHER PUBLICATIONS

PCT/US2014/029605, Jul. 23, 2014, International Search Report and Written Opinion.
PCT/US2014/029665, Jul. 23, 2014, International Search Report and Written Opinion.
PCT/US2014/029710, Jul. 25, 2014, International Search Report and Written Opinion.
PCT/US2014/029062, Sep. 17, 2014, International Search Report and Written Opinion.
PCT/US2014/029750, Oct. 2, 2014, International Search Report and Written Opinion.
PCT/US2014/029408, Jun. 17, 2014, International Search Report and Written Opinion.
PCT/US2015/050659, Dec. 21, 2015, International Search Report and Written Opinion.
PCT/US2015/050750, Nov. 19, 2015, Invitation to Pay Additional Fees and, Where Applicable, Protest Fee.
PCT/US2015/050750, Feb. 3, 2016, International Search Report and Written Opinion.
PCT/US2015/050675, Dec. 17, 2015, International Search Report and Written Opinion.
PCT/US2015/050629, Jun. 30, 2016, International Search Report and Written Opinion.
International Search Report and Written Opinion for International Application No. PCT/US2014/029009 dated May 28, 2014.
International Search Report and Written Opinion for International Application No. PCT/US2014/029160 dated May 28, 2014.
International Search Report and Written Opinion for International Application No. PCT/US2014/029583 dated Jul. 29, 2014.
International Search Report and Written Opinion for International Application No. PCT/US2014/029605 dated Jul. 23, 2014.
International Search Report and Written Opinion for International Application No. PCT/US2014/029665 dated Jul. 23, 2014.
International Search Report and Written Opinion for International Application No. PCT/US2014/029710 dated Jul. 15, 2014.
International Search Report and Written Opinion for International Application No. PCT/US2014/029062 dated Sep. 17, 2014.
International Search Report and Written Opinion for International Application No. PCT/US2014/029750 dated Oct. 2, 2014.
International Search Report and Written Opinion for International Application No. PCT/US2014/029408 dated Jun. 17, 2014.
International Search Report and Written Opinion for International Application No. PCT/US2015/050675 dated Dec. 17, 2015.
International Search Report and Written Opinion for International Application No. PCT/US2015/050659 dated Dec. 21, 2015.
Invitation to Pay Additional Fees, and Where Applicable, Protest Fee for International Application No. PCT/US2015/050750 dated Nov. 19, 2015.
International Search Report and Written Opinion for International Application No. PCT/US2015/050750 dated Feb. 3, 2016.
International Search Report and Written Opinion for International Application No. PCT/US2015/050629 dated Jun. 30, 2016.
CAS Registry Accession No. 1340581-60-3. Nov. 3, 2011.
CAS Registry Accession No. 1342545-59-8. Nov. 8, 2011.
CAS Registry File RN 1524901-21-0, STN Entry Date: Oct. 10, 2013.
CAS Registry File RN 1547978-57-3, STN Entry Date: Jul. 3, 2013.
CAS Registry File RN 1551294-59-7, STN Entry Date: Oct. 10, 2013.
CAS Registry File RN 1564967-49-2, STN Entry Date: Oct. 10, 2013.
CAS Registry File RN 1564977-15-6, STN Entry Date: Oct. 10, 2013.
CAS Registry File RN 1565645-75-1. Dated Mar. 10, 2014.
CAS Registry File RN 1566071-28-0, STN Entry Date: Oct. 10, 2013.
CAS Registry File RN 1566350-70-6, STN Entry Date: Oct. 10, 2013.
CAS Registry Files RN 1179596-03-2 and RN 1179823-36-9, STN Entry Date: Sep. 3, 2009.
PubChem Submission; NIH/NCBI, Substance Identifier 107215563. Akos Consulting & Solutions. Feb. 22, 2011. 6 pages.
PubChem Submission; NIH/NCBI, Substance Identifier 151630580. Akos Consulting & Solutions. Oct. 24, 2012. 10 pages.
PubChem Submission; NIH/NCBI, Compound Identifier 62687207. Oct. 22, 2012. 9 pages.
PubChem Submission; NIH/NCBI, Compound Identifier 65237285. Oct. 23, 2012. 9 pages.
PubChem Submission; NIH/NCBI, Compound Identifier 1170606. Jul. 10, 2005. 10 pages.
PubChem Submission; NIH/NCBI, Compound Identifier 51623447. May 20, 2011. 10 pages.
PubChem Submission; NIH/NCBI, Compound Identifier 72853360. Feb. 28, 2014. 10 pages.
PubChem Submission; NIH/NCBI, Compound Identifier 46961966. Nov. 25, 2010. 9 pages.
Al-Dhaheri et al., CARM1 is an important determinant of ERα-dependent breast cancer cell differentiation and proliferation in breast cancer cells. Cancer Res. Mar. 15, 2011;71(6):2118-28. doi: 10.1158/0008-5472.CAN-10-2426. Epub Jan. 31, 2011.
Blanchet et al., CD28 costimulatory signal induces protein arginine methylation in T cells. J Exp Med. Aug. 1, 2005;202(3):371-7.
Boger, Asymmetric dimethylarginine (ADMA): a novel risk marker in cardiovascular medicine and beyond. Ann Med. 2006;38(2):126-36.
Bratenko et al., Synthesis and antimicrobial activities of 1,3-bis(4-pyrazolylmethyl)-2-(4-nitrophenyl) imidazolidines and hexahydropyrimidines. Farmatsevtichnii Zhurnal. 2007;5:66-70.
Chen et al., Expression of nitric oxide related enzymes in coronary heart disease. Basic Res Cardiol. Jul. 2006;101(4):346-53. Epub May 16, 2006.
Cheung et al., Protein arginine-methyltransferase-dependent oncogenesis. Nat Cell Biol. Oct. 2007;9(10):1208-15. Epub Sep. 23, 2007.
Choi et al., Protein arginine methyltransferase 1 regulates hepatic glucose production in a FoxO1-dependent manner. Hepatology. Oct. 2012;56(4):1546-56. doi: 10.1002/hep.25809.
Copeland, Protein methyltransferase inhibitors as personalized cancer therapeutics. Drug Discov Today Ther Strateg. 2012;9:e83-e90.
Cornelison, Human papillomavirus genotype 16 vaccines for cervical cancer prophylaxis and treatment. Curr Opin Oncol. Sep. 2000;12(5):466-73.
Covic et al., Arginine methyltransferase CARM1 is a promoter-specific regulator of NF-kappaB-dependent gene expression. EMBO J. Jan. 12, 2005;24(1):85-96. Epub Dec. 16, 2004.
Davies et al., Oculopharyngeal muscular dystrophy: potential therapies for an aggregate-associated disorder. Int J Biochem Cell Biol. 2006;38(9):1457-62. Epub Feb. 28, 2006.
Dermer, Another Anniversary for the War on Cancer. Bio/Tehcnology. 1994;12:320.
Engelmann et al., The dark side of E2F1: in transit beyond apoptosis. Cancer Res. Feb. 1, 2012;72(3):571-5. doi: 10.1158/0008-5472.CAN-11-2575.
Forbes et al., COSMIC: mining complete cancer genomes in the Catalogue of Somatic Mutations in Cancer. Nucleic Acids Res. Jan. 2011;39(Database issue):D945-50. doi: 10.1093/nar/gkq929. Epub Oct. 15, 2010.
Freshney, Culture of Animal Cells: A Manual of Basic Technique. John Wiley and Sons. 2005, 5th Ed., p. 8.
Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.
Fuchi et al., A library synthesis of pyrazoles by azomethine imine cycloaddition to the polymer-supported vinylsulfone. Chem Lett. 2005;34(3):438-9.
Hong et al., Aberrant expression of CARM1, a transcriptional coactivator of androgen receptor, in the development of prostate carcinoma and androgen-independent status. Cancer. Jul. 1, 2004;101(1):83-9.
Ito et al., A medium-term rat liver bioassay for rapid in vivo detection of carcinogenic potential of chemicals. Cancer Sci. Jan. 2003;94(1):3-8. Review.

(56) References Cited

OTHER PUBLICATIONS

Jacobi et al., Asymmetrical dimethylarginine in renal disease: limits of variation or variation limits? A systematic review. Am J Nephrol. 2008;28(2):224-37. Epub Oct. 24, 2007.
Kleinschmidt et al., Cell cycle regulation by the PRMT6 arginine methyltransferase through repression of cyclin-dependent kinase inhibitors. PLoS One. 2012;7(8):e41446. doi: 10.1371/journal.pone.0041446. Epub Aug. 20, 2012.
Le Romancer et al., Methylation, a key step for nongenomic estrogen signaling in breast tumors. Steroids. Aug.-Sep. 2010;75(8-9):560-4. doi: 10.1016/j.steroids.2010.01.013. Epub Jan. 29, 2010.
Le Romancer et al., Regulation of estrogen rapid signaling through arginine methylation by PRMT1. Mol Cell. Jul. 25, 2008;31(2):212-21. doi: 10.1016/j.molcel.2008.05.025.
Leovac et al., Copper(II) complexes with reduced Schiff base: Synthesis, spectroscopic, thermal, X-ray, and cytotoxic studies of novel copper(II) complexes with an arylpyrazole ligand. Austrailian J Chem. 2007;60(8):615-20.
Majumder et al., Involvement of arginine methyltransferase CARM1 in androgen receptor function and prostate cancer cell viability. Prostate. Sep. 1, 2006;66(12):1292-301.
Michaud-Levesque et al., Thrombospondin-1 is a transcriptional repression target of PRMT6. J Biol Chem. Aug. 7, 2009;284(32):21338-46. doi: 10.1074/jbc.M109.005322. Epub Jun. 9, 2009.
Nagahata et al., Expression profiling to predict postoperative prognosis for estrogen receptor-negative breast cancers by analysis of 25,344 genes on a cDNA microarray. Cancer Sci. Mar. 2004;95(3):218-25.
Perreault et al., Regulation of the nuclear poly(A)-binding protein by arginine methylation in fission yeast. J Biol Chem. Mar. 9, 2007;282(10):7552-62. Epub Jan. 9, 2007.
Rappsilber et al., Detection of arginine dimethylated peptides by parallel precursor ion scanning mass spectrometry in positive ion mode. Anal Chem. Jul. 1, 2003;75(13):3107-14.
Richard et al., Arginine methylation regulates IL-2 gene expression: a role for protein arginine methyltransferase 5 (PRMT5). Biochem J. May 15, 2005;388(Pt 1):379-86.
Seligson et al., Global histone modification patterns predict risk of prostate cancer recurrence. Nature. Jun. 30, 2005;435(7046):1262-6.
Shia et al., PRMT1 interacts with AML1-ETO to promote its transcriptional activation and progenitor cell proliferative potential. Blood. May 24, 2012;119(21):4953-62. doi: 10.1182/blood-2011-04-347476. Epub Apr. 12, 2012.
Singh et al., DAL-1/4.1B tumor suppressor interacts with protein arginine N-methyltransferase 3 (PRMT3) and inhibits its ability to methylate substrates in vitro and in vivo. Oncogene. Oct. 14, 2004;23(47):7761-71.
Sydow et al., Insulin resistance: potential role of the endogenous nitric oxide synthase inhibitor ADMA. Vasc Med. Jul. 2005;10 Suppl 1:S35-43.
Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.
Vallance et al., Accumulation of an endogenous inhibitor of nitric oxide synthesis in chronic renal failure. Lancet. Mar. 7, 1992;339(8793):572-5.
Vallance et al., Endogenous dimethylarginine as an inhibitor of nitric oxide synthesis. J Cardiovasc Pharmacol. 1992;20 Suppl 12:S60-2.
Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.
Wang et al., CARM1/PRMT4 is necessary for the glycogen gene expression programme in skeletal muscle cells. Biochem J. Jun. 1, 2012;444(2):323-31. doi: 10.1042/BJ20112033.
Yoshimatsu et al., Dysregulation of PRMT1 and PRMT6, Type I arginine methyltransferases, is involved in various types of human cancers. Int J Cancer. Feb. 1, 2011;128(3):562-73. doi: 10.1002/ijc.25366.
Zakrzewicz et al., From arginine methylation to ADMA: a novel mechanism with therapeutic potential in chronic lung diseases. BMC Pulm Med. Jan. 29, 2009;9:5. doi: 10.1186/1471-2466-9-5.
Invitation to Pay Additional Fees, and Where Applicable, Protest Fee for International Application No. PCT/US2017/016472 dated Apr. 4, 2017.
International Search Report and Written Opinion for International Application No. PCT/US2017/016472 dated Jun. 5, 2017.
PubChem Submission; NIH/NCBI Substance Identifier 66148168. Oct. 24, 2010. 9 pages.
U.S. Appl. No. 14/212,057, filed Mar. 14, 2014, Granted, U.S. Pat. No. 8,952,026.
U.S. Appl. No. 14/775,175, filed Sep. 11, 2015, Published, 2016-0039767.
U.S. Appl. No. 14/212,354, filed Mar. 14, 2014, Granted, U.S. Pat. No. 9,023,883.
U.S. Appl. No. 14/675,781, filed Apr. 1, 2015, Granted, U.S. Pat. No. 9,475,776.
U.S. Appl. No. 14/775,232, filed Sep. 11, 2015, Published, 2016-0137609.
U.S. Appl. No. 15/093,103, filed Apr. 7, 2016, Granted, U.S. Pat. No. 9,732,041.
U.S. Appl. No. 14/697,420, filed Apr. 27, 2015, Granted, U.S. Pat. No. 9,440,950.
U.S. Appl. No. 14/212,713, filed Mar. 14, 2014, Granted, U.S. Pat. No. 9,133,189.
U.S. Appl. No. 14/808,270, filed Jul. 24, 2015, Granted, U.S. Pat. No. 9,630,961.
U.S. Appl. No. 14/212,543, filed Mar. 14, 2014, Granted, U.S. Pat. No. 9,120,757.
U.S. Appl. No. 14/808,290, filed Jul. 24, 2015, Published, 2016-0184267.
U.S. Appl. No. 14/775,794, filed Sep. 14, 2015, Granted, U.S. Pat. No. 9,598,374.
U.S. Appl. No. 14/213,272, filed Mar. 14, 2014, Granted, U.S. Pat. No. 9,365,527.
U.S. Appl. No. 14/775,213, filed Sep. 11, 2015, Published, 2016-0031839.
U.S. Appl. No. 15/150,772, filed May 10, 2016, Published, 2017-0088529.
U.S. Appl. No. 14/213,144, filed Mar. 14, 2014, Granted, U.S. Pat. No. 9,394,258.
U.S. Appl. No. 14/775,246, filed Sep. 11, 2015, Published, 2016-0024017.
U.S. Appl. No. 15/178,696, filed Jun. 10, 2016, Published, 2017-0119735.
U.S. Appl. No. 14/212,965, filed Mar. 14, 2014, Granted, U.S. Pat. No. 9,447,079.

* cited by examiner

PRMT1 INHIBITORS AND USES THEREOF

RELATED APPLICATIONS

The present application is a divisional of and claims priority under 35 U.S.C. § 120 to U.S. patent application, U.S. Ser. No. 14/212,965, filed Mar. 14, 2014, which claims priority under 35 U.S.C. § 119(e) to U.S. Provisional Patent Application, U.S. Ser. No. 61/781,055, filed Mar. 14, 2013, the entire contents of each of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., PRMT1), many of which are associated with specific genetic alterations that can cause human disease.

Disease-associated chromatin-modifying enzymes (e.g., PRMT1) play a role in diseases such as proliferative disorders, autoimmune disorders, muscular disorders, vascular disorders, metabolic disorders, and neurological disorders. Thus, there is a need for the development of small molecules that are capable of inhibiting the activity of PRMT1.

DETAILED DESCRIPTION OF CERTAIN EMBODIMENTS

PRMT1 is an attractive target for modulation given its role in the regulation of diverse biological processes. It has now been found that compounds described herein, and pharmaceutically acceptable salts and compositions thereof, are effective as inhibitors of PRMT1. Such compounds have the general Formula (I-a) or (I-b):

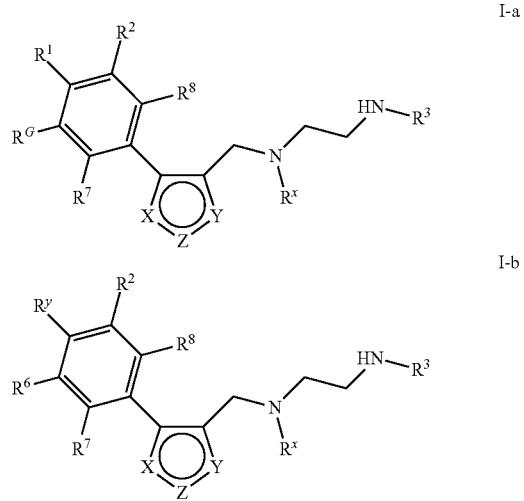

or a pharmaceutically acceptable salt thereof, wherein X, Y, Z, $R^x$, $R^y$, $R^G$, $R^1$, $R^2$, $R^3$, $R^6$, $R^7$, and $R^8$ are as defined herein.

In some embodiments, pharmaceutical compositions are provided which comprise a compound described herein (e.g., a compound of Formula (I-a) or (I-b)), or a pharmaceutically acceptable salt thereof, and optionally a pharmaceutically acceptable excipient.

In certain embodiments, compounds described herein inhibit activity of PRMT1. In certain embodiments, methods of inhibiting PRMT1 are provided which comprise contacting PRMT1 with an effective amount of a compound of Formula (I-a) or (I-b), or a pharmaceutically acceptable salt thereof. The PRMT1 may be purified or crude, and may be present in a cell, tissue, or a subject. Thus, such methods encompass inhibition of PRMT1 activity both in vitro and in vivo. In certain embodiments, the PRMT1 is wild-type PRMT1. In certain embodiments, the PRMT1 is overexpressed. In certain embodiments, the PRMT1 is a mutant. In certain embodiments, the PRMT1 is in a cell. In certain embodiments, the PRMT1 is in an animal, e.g., a human. In some embodiments, the PRMT1 is expressed at normal levels in a subject, but the subject would benefit from PRMT1 inhibition (e.g., because the subject has one or more mutations in an PRMT1 substrate that causes an increase in methylation of the substrate with normal levels of PRMT1). In some embodiments, the PRMT1 is in a subject known or identified as having abnormal PRMT1 activity (e.g., overexpression). In some embodiments, a provided compound is selective for PRMT1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective relative to one or more other methyltransferases.

In certain embodiments, methods of modulating gene expression in a cell are provided which comprise contacting a cell with an effective amount of a compound of Formula (I-a) or (I-b), or a pharmaceutically acceptable salt thereof, or a pharmaceutical composition thereof. In certain embodiments, the cell in culture in vitro. In certain embodiments, cell is in an animal, e.g., a human.

In certain embodiments, methods of modulating transcription in a cell are provided which comprise contacting a cell with an effective amount of a compound of Formula (I-a) or (I-b), or a pharmaceutically acceptable salt thereof, or a pharmaceutical composition thereof. In certain embodiments, the cell in culture in vitro. In certain embodiments, the cell is in an animal, e.g., a human.

In some embodiments, methods of treating a PRMT1-mediated disorder are provided which comprise administering to a subject suffering from a PRMT1-mediated disorder an effective amount of a compound described herein (e.g., a compound of Formula (I-a) or (I-b)), or a pharmaceutically acceptable salt thereof, or a pharmaceutical composition thereof. In certain embodiments, the PRMT1-mediated disorder is a proliferative disorder. In certain embodiments, compounds described herein are useful for treating cancer. In certain embodiments, compounds described herein are useful for treating breast cancer, prostate cancer, lung cancer, colon cancer, bladder cancer, or leukemia. In certain embodiments, the PRMT1-mediated disorder is a muscular disorder. In certain embodiments, the PRMT1-mediated disorder is an autoimmune disorder. In certain embodiments, the PRMT1-mediated disorder is a neurological disorder. In certain embodiments, the PRMT1-mediated disorder is a vascular disorder. In certain embodiments, the PRMT1-mediated disorder is a metabolic disorder.

Compounds described herein are also useful for the study of PRMT1 in biological and pathological phenomena, the It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form.

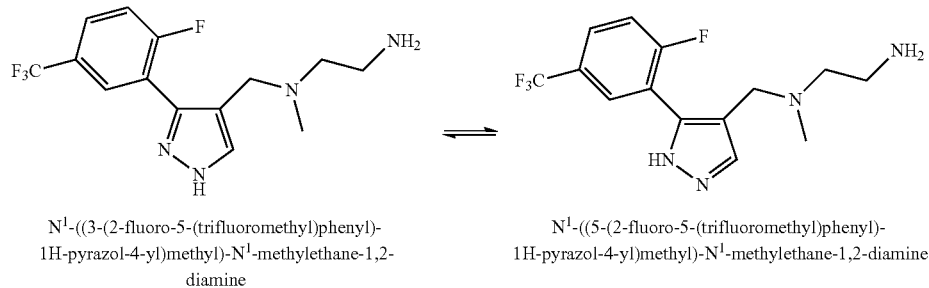 [SMILES: CN(CCN)Cc1c[nH]nc1-c1cc(C(F)(F)F)ccc1F ; CN(CCN)Cc1cn[nH]c1-c1cc(C(F)(F)F)ccc1F]

N¹-((3-(2-fluoro-5-(trifluoromethyl)phenyl)-1H-pyrazol-4-yl)methyl)-N¹-methylethane-1,2-diamine N¹-((5-(2-fluoro-5-(trifluoromethyl)phenyl)-1H-pyrazol-4-yl)methyl)-N¹-methylethane-1,2-diamine study of intracellular signal transduction pathways mediated by PRMT1, and the comparative evaluation of new PRMT1 inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 20 carbon atoms and one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

As used herein, "alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary 5,6-bicyclic heteroaryl groups include, without limitation, any one of the following formulae:

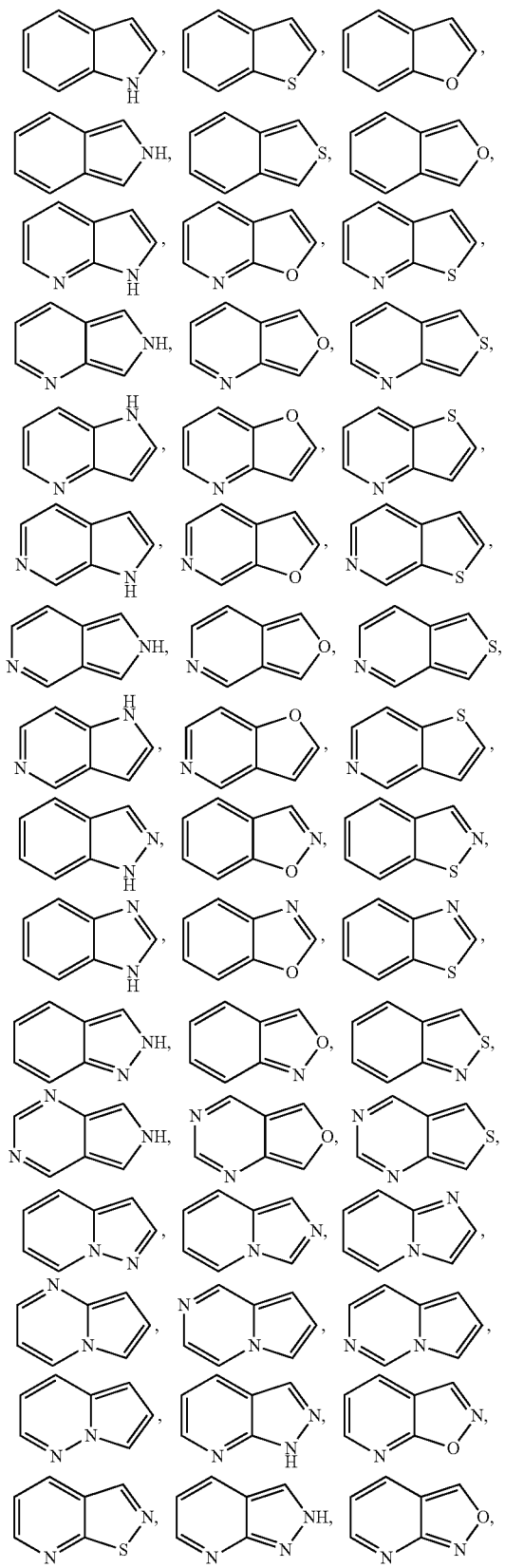

-continued
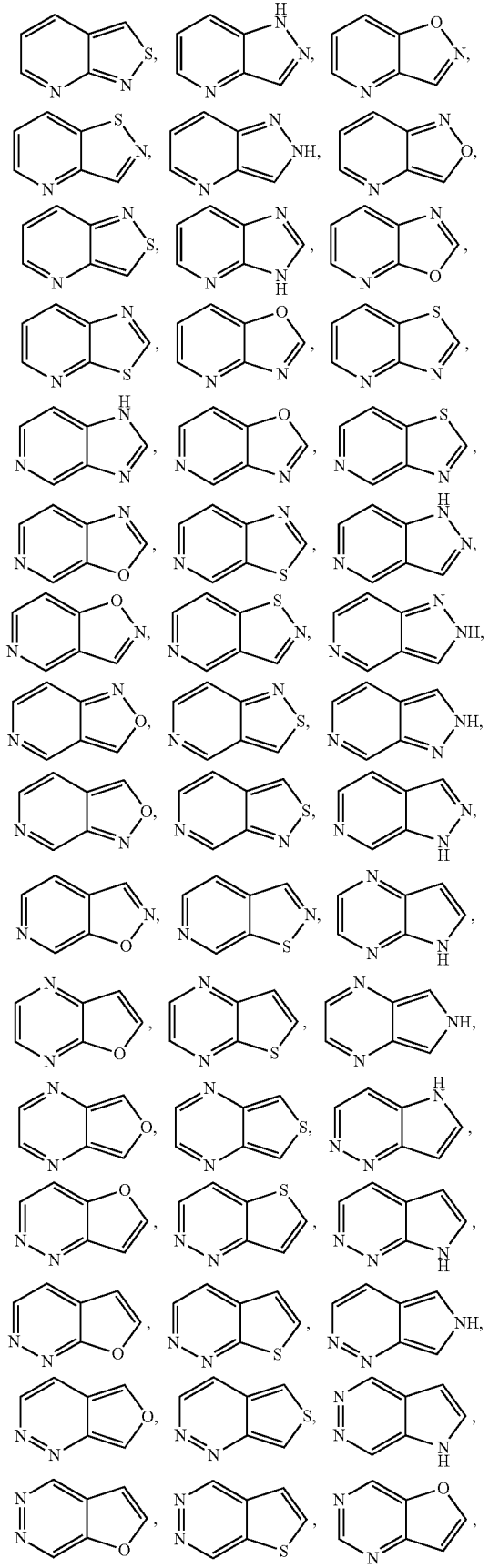
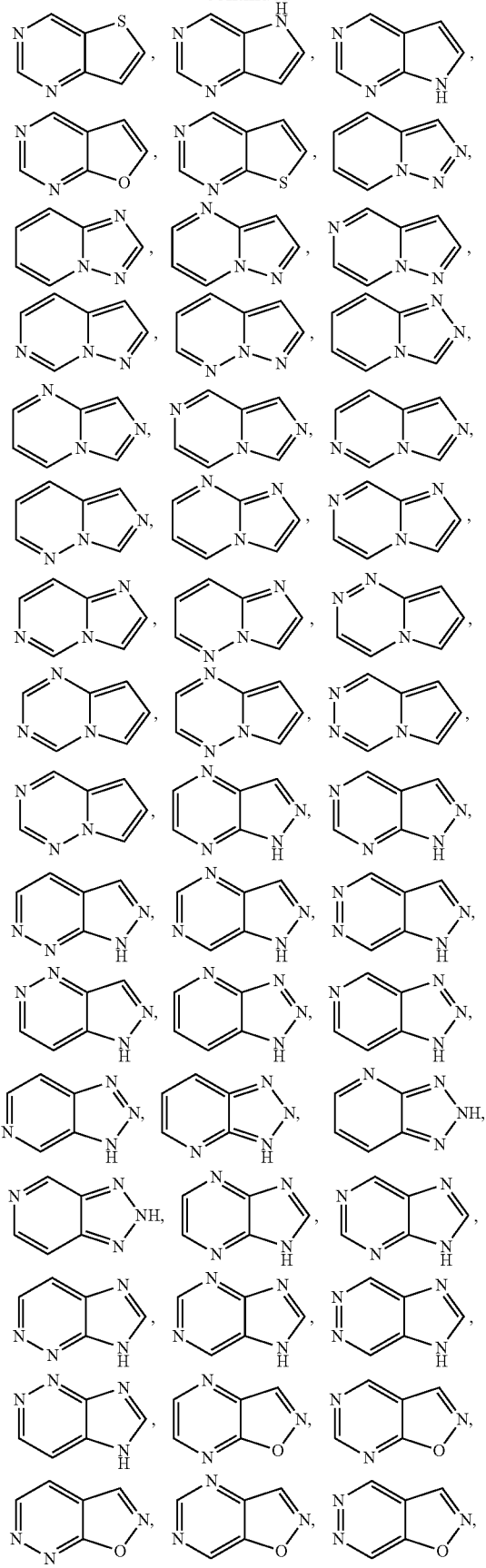

-continued

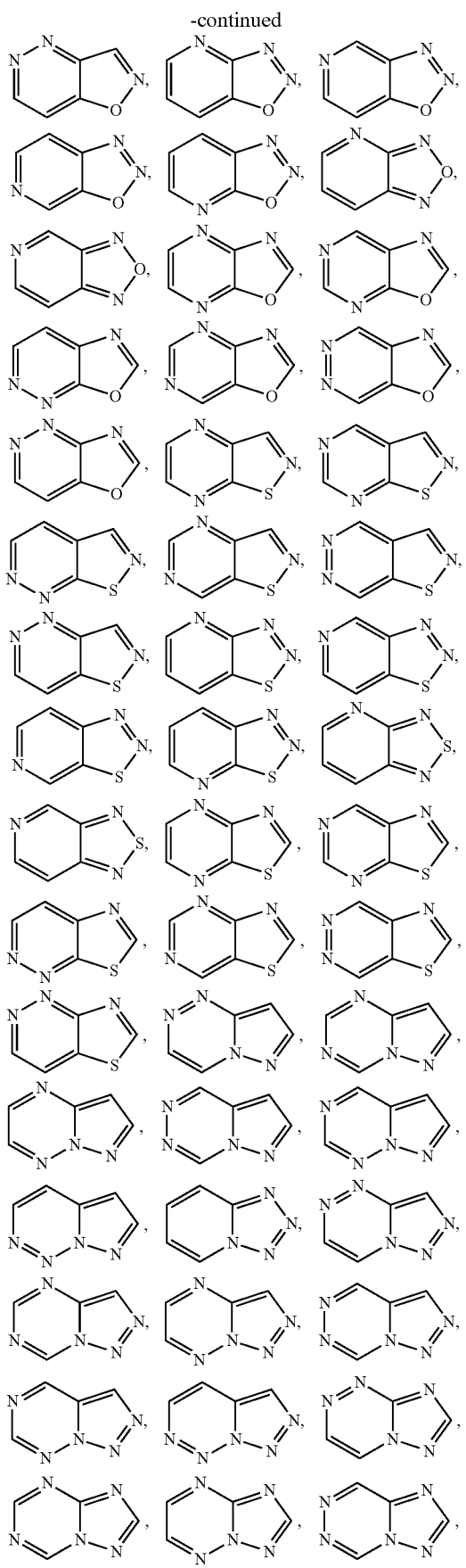
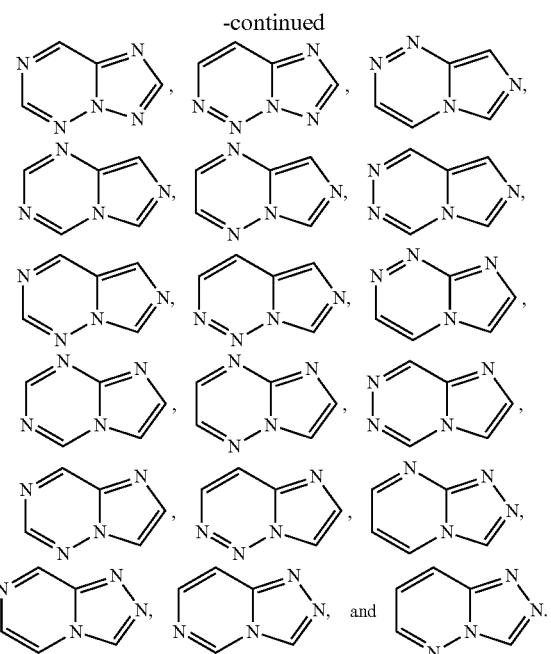

In any of the monocyclic or bicyclic heteroaryl groups, the point of attachment can be any carbon or nitrogen atom, as valency permits.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$alkyl)$_2$, —N(C$_{1-6}$ alkyl)$_2$, —N(C$_{1-6}$ alkyl)$_3$$^+$X$^-$, —NH(C$_{1-6}$alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-4}$ alkyl), —SO$_2$NH$_2$, —SO$_2$C$_{1-4}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-4}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{C}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, co-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methyltransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as PRMT1 inhibitors. In some embodiments, the present disclosure provides a compound of Formula (I-a) or (I-b):

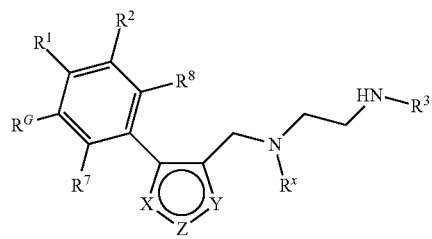

I-a

I-b

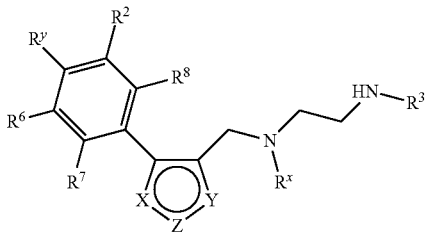

or a pharmaceutical salt thereof,
wherein
X is N, Z is $NR^4$, and Y is $CR^5$; or
X is $NR^4$, Z is N, and Y is $CR^5$; or
X is $CR^5$, Z is $NR^4$, and Y is N; or
X is $CR^5$, Z is N, and Y is $NR^4$;
$R^G$ is $-CF_3$ or $-CF_2H$;
$R^1$ is hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —(CR$^z$R$^z$)$_n$C(O)N(R$^B$)$_2$, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;
$R^2$ is hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;
$R^6$ is hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;
$R^7$ and $R^8$ are independently selected from the group consisting of hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$; wherein at least one of $R^7$ and $R^8$ is not hydrogen;
each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;
each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or two $R^B$ groups are taken together with their intervening atoms to form an optionally substituted heterocyclic ring;
$R^1$ and $R^2$ are optionally taken together to form a carbocyclic, heterocyclic, or aryl ring; or
$R^2$ and $R^8$ are optionally taken together to form a carbocyclic, heterocyclic, or aryl ring; or
$R^6$ and $R^7$ are optionally taken together to form a carbocyclic, heterocyclic, or aryl ring;
$R^3$ is hydrogen, $C_{1-4}$ alkyl, or $C_{3-4}$ cycloalkyl;
$R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy;
Cy is optionally substituted $C_{3-7}$ cycloalkyl, optionally substituted 4- to 7-membered heterocyclyl, optionally substituted aryl, or optionally substituted heteroaryl;
$R^5$ is hydrogen, halo, —CN, optionally substituted $C_{1-4}$ alkyl, or optionally substituted $C_{3-4}$ cycloalkyl;
$R^x$ is optionally substituted $C_{1-4}$ alkyl or optionally substituted $C_{3-4}$ cycloalkyl;
$R^y$ is —NR$^B$C(O)R$^A$, —NR$^B$SO$_2$R$^A$, or —(CR$^z$R$^z$)$_n$C(O)N(R$^B$)$_2$;
each $R^z$ is independently hydrogen or fluoro; and
n is 0, 1, 2, 3, or 4.
In certain embodiments, a provided compound is of Formula (II-a):

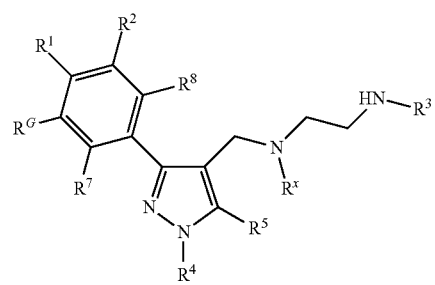

II-a or a pharmaceutically acceptable salt thereof, wherein $R^G$, $R^1$, $R^2$, $R^3$, $R^4$, $R^5$, $R^7$, $R^8$, and $R^x$ are as described herein.
In certain embodiments, a provided compound is of Formula (II-b):

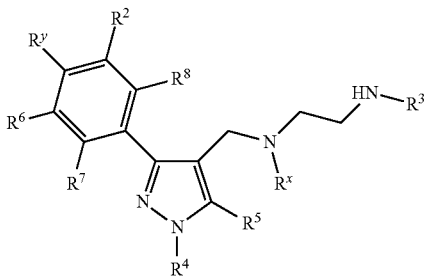

II-b or a pharmaceutically acceptable salt thereof, wherein $R^y$, $R^2$, $R^3$, $R^4$, $R^5$, $R^6$, $R^7$, $R^8$, and $R^x$ are as described herein.

In certain embodiments, a provided compound is of Formula (III-a):

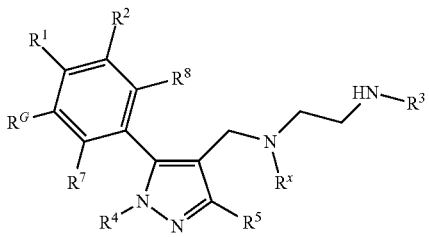

III-a or a pharmaceutically acceptable salt thereof, wherein $R^G$, $R^1$, $R^2$, $R^3$, $R^4$, $R^5$, $R^7$, $R^8$, and $R^x$ are as described herein.

In certain embodiments, a provided compound is of Formula (III-b):

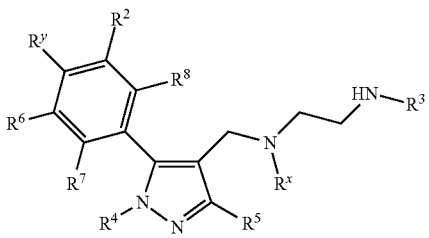

III-b or a pharmaceutically acceptable salt thereof, wherein $R^y$, $R^2$, $R^3$, $R^4$, $R^5$, $R^6$, $R^7$, $R^8$, and $R^x$ are as described herein.

In certain embodiments, a provided compound is of Formula (IV-a):

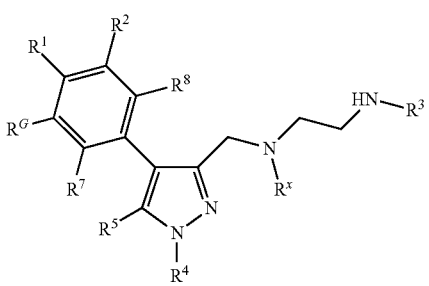

IV-a or a pharmaceutically acceptable salt thereof, wherein $R^G$, $R^1$, $R^2$, $R^3$, $R^4$, $R^5$, $R^7$, R, and $R^x$ are as described herein.

In certain embodiments, a provided compound is of Formula (IV-b):

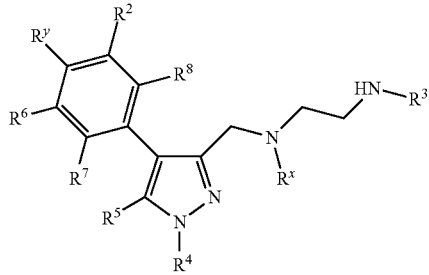

IV-b or a pharmaceutically acceptable salt thereof, wherein $R^y$, $R^2$, $R^3$, $R^4$, $R^5$, $R^6$, $R^7$, $R^8$, and $R^x$ are as described herein.

In certain embodiments, a provided compound is of Formula (V-a):

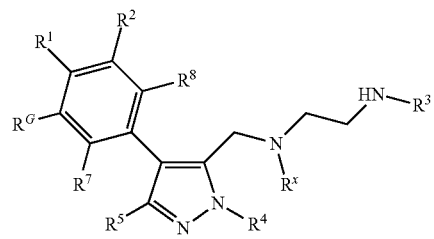

V-a or a pharmaceutically acceptable salt thereof, wherein $R^G$, $R^1$, $R^2$, $R^3$, $R^4$, $R^5$, $R^7$, $R^8$, and $R^x$ are as described herein.

In certain embodiments, a provided compound is of Formula (V-b):

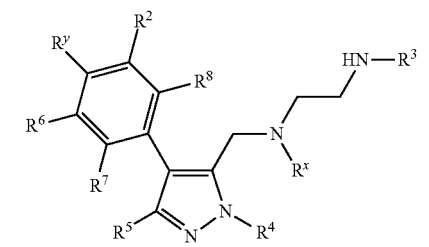

V-b or a pharmaceutically acceptable salt thereof, wherein $R^y$, $R^2$, $R^3$, $R^4$, $R^5$, $R^6$, $R^7$, $R^8$, and $R^x$ are as described herein.

In certain embodiments, a provided compound is of Formula (VI):

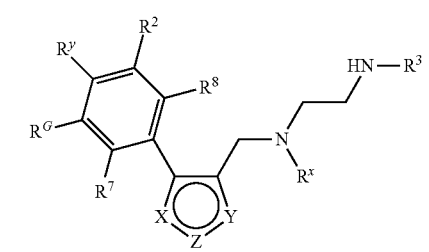

VI or a pharmaceutically acceptable salt thereof, wherein $R^G$, $R^y$, $R^2$, $R^3$, $R^7$, $R^8$, and $R^x$ are as described herein.

In certain embodiments, $R^1$ is hydrogen and $R^2$ is not hydrogen. In certain embodiments, $R^1$ is not hydrogen and $R^2$ is hydrogen. In certain embodiments, $R^1$ and $R^2$ are hydrogen. In certain embodiments, $R^1$ and $R^2$ are not hydrogen.

In certain embodiments, $R^6$ is hydrogen and $R^2$ is not hydrogen. In certain embodiments, $R^6$ is not hydrogen and $R^2$ is hydrogen. In certain embodiments, $R^6$ and $R^2$ are hydrogen. In certain embodiments, $R^6$ and $R^2$ are not hydrogen.

As defined generally above, $R^y$ is $-NR^BC(O)R^A$, $-NR^BSO_2R^A$, or $-(CR^zR^z)_nC(O)N(R^B)_2$. In certain embodiments, $R^y$ is $-NR^BC(O)R^A$. In certain embodiments, $R^y$ is $-NHC(O)R^A$. In certain embodiments, $R^y$ is $-NR^BC(O)R^A$ or $-NHC(O)R^A$, wherein $R^A$ is optionally substituted alkyl. In certain embodiments, $R^y$ is $-NR^BC(O)R^A$ or $-NHC(O)R^A$, wherein $R^A$ is alkoxyalkyl. In certain embodiments, $R^y$ is $-NR^BC(O)R^A$ or $-NHC(O)R^A$, wherein $R^A$ is optionally substituted alkenyl. In certain embodiments, $R^y$ is $-NR^BC(O)R^A$ or $-NHC(O)R^A$, wherein $R^A$ is unsubstituted $C_{1-6}$ alkyl. In certain embodiments, $R^y$ is $-NR^BSO_2R^A$. In certain embodiments, $R^y$ is $-NHSO_2R^A$. In certain embodiments, $R^y$ is $-NR^BSO_2R^A$ or $-NHSO_2R^A$, wherein $R^A$ is optionally substituted alkyl. In certain embodiments, $R^y$ is $-NR^BSO_2R^A$ or $-NHSO_2R^A$, wherein $R^A$ is alkoxyalkyl. In certain embodiments, $R^y$ is $-NR^BSO_2R^A$ or $-NHSO_2R^A$, wherein $R^A$ is optionally substituted alkenyl. In certain embodiments, $R^y$ is $-NR^BSO_2R^A$ or $-NHSO_2R^A$, wherein $R^A$ is unsubstituted $C_{1-6}$ alkyl. In certain embodiments, $R^y$ is $-(CR^zR^z)_nC(O)N(R^B)_2$. In certain embodiments, $R^y$ is $-CH_2C(O)N(R^B)_2$. In certain embodiments, $R^y$ is $-(CR^zR^z)_nC(O)N(R^B)_2$ or $-CH_2C(O)N(R^B)_2$, wherein $R^A$ is optionally substituted alkyl. In certain embodiments, $R^y$ is $-(CR^zR^z)_nC(O)N(R^B)_2$ or $-CH_2C(O)N(R^B)_2$, wherein $R^A$ is alkoxyalkyl. In certain embodiments, $R^y$ is $-(CR^zR^z)_nC(O)N(R^B)_2$ or $-CH_2C(O)N(R^B)_2$, wherein $R^A$ is optionally substituted alkenyl. In certain embodiments, $R^y$ is $-(CR^zR^z)_nC(O)N(R^B)_2$ or $-CH_2C(O)N(R^B)_2$, wherein $R^A$ is unsubstituted $C_{1-6}$ alkyl. In certain embodiments, each $R^z$ is hydrogen. In certain embodiments, n is 0. In certain embodiments, n is 1. In certain embodiments, n is 2. In certain embodiments, n is 3. In certain embodiments, n is 4. In some embodiments, $R^A$ is optionally substituted $C_{1-6}$ alkyl. In some embodiments, $R^A$ is $C_{1-4}$ alkyl. In some embodiments, $R^A$ is $C_{2-4}$ alkenyl. In some embodiments, $R^A$ is $C_{2-4}$ alkynyl. In some embodiments, $R^B$ is optionally substituted $C_{1-6}$ alkyl. In some embodiments, $R^B$ is $C_{1-4}$ alkyl. In some embodiments, $R^B$ is $C_{2-4}$ alkenyl. In some embodiments, $R^B$ is $C_{2-4}$ alkynyl.

As defined generally above, $R^1$ is hydrogen, halo, $-CN$, $-NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, $-(CR^zR^z)_nC(O)N(R^B)_2$, $-OR^A$, $-N(R^B)_2$, $-SR^A$, $-C(=O)R^A$, $-C(O)OR^A$, $-C(O)SR^A$, $-C(O)N(R^B)_2$, $-C(O)N(R^B)N(R^B)_2$, $-OC(O)R^A$, $-OC(O)N(R^B)_2$, $-NR^BC(O)R^A$, $-NR^BC(O)N(R^B)_2$, $-NR^BC(O)N(R^B)N(R^B)_2$, $-NR^BC(O)OR^A$, $-SC(O)R^A$, $-C(=NR^B)R^A$, $-C(=NNR^B)R^A$, $-C(=NOR^A)R^A$, $-C(=NR^B)N(R^B)_2$, $-NR^BC(=NR^B)R^B$, $-C(=S)R^A$, $-C(=S)N(R^B)_2$, $-NR^BC(=S)R^A$, $-S(O)R^A$, $-OS(O)_2R^A$, $-SO_2R^A$, $-NR^BSO_2R^A$, or $-SO_2N(R^B)_2$. In certain embodiments, $R^1$ is hydrogen. In some embodiments, $R^1$ is not hydrogen. In some embodiments, $R^1$ is halo. In certain embodiments, $R^1$ is fluoro. In certain embodiments, $R^1$ is chloro. In some embodiments, $R^1$ is optionally substituted alkyl, optionally substituted alkenyl, optionally substituted alkynyl, or optionally substituted carbocyclyl. In certain embodiments, $R^1$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^1$ is optionally substituted $C_{1-6}$ alkyl. In certain embodiments, $R^1$ is substituted $C_{1-6}$ alkyl. In certain embodiments, $R^1$ is $-CF_3$, $CHF_2$, or $CH_2F$. In certain embodiments, $R^1$ is $-C_{1-6}$ alkyl-carbocyclyl. In certain embodiments, $R^1$ is $-CH_2$-cyclopropyl or $-CH_2$-cyclobutyl. In certain embodiments, $R^1$ is unsubstituted $C_{1-6}$ alkyl. In certain embodiments, $R^1$ is methyl, ethyl, propyl, butyl, or pentyl. In certain embodiments, $R^1$ is isopropyl, isobutyl, or isoamyl. In certain embodiments, $R^1$ is isobutyl. In some embodiments, $R^1$ is $-CN$. In some embodiments, $R^1$ is optionally substituted carbocyclyl, optionally substituted aryl, optionally substituted heterocyclyl, or optionally substituted heteroaryl. In some embodiments, $R^1$ is $-OR^A$, $-N(R^B)_2$, $-SR^A$, $-C(=O)R^A$, $-C(O)OR^A$, $-C(O)SR^A$, $-C(O)N(R^B)_2$, $-C(O)N(R^B)N(R^B)_2$, $-OC(O)R^A$, $-OC(O)N(R^B)_2$, $-NR^BC(O)R^A$, $-NR^BC(O)N(R^B)_2$, $-NR^BC(O)N(R^B)N(R^B)_2$, $-NR^BC(O)OR^A$, $-SC(O)R^A$, $-C(=NR^B)R^A$, $-C(=NNR^B)R^A$, $-C(=NOR^A)R^A$, $-C(=NR^B)N(R^B)_2$, $-NR^BC(=NR^B)R^B$, $-C(=S)R^A$, $-C(=S)N(R^B)_2$, $-NR^BC(=S)R^A$, $-S(O)R^A$, $-OS(O)_2R^A$, $-SO_2R^A$, $-NR^BSO_2R^A$, or $-SO_2N(R^B)_2$. In certain embodiments, $R^1$ is $-N(R^B)_2$. In certain embodiments, $R^1$ is $-NHR^B$. In certain embodiments, $R^1$ is $-NH_2$. In certain embodiments, $R^1$ is $-OR^A$. In certain embodiments, $R^1$ is $-OH$. In certain embodiments, $R^1$ is $-OR^A$, wherein $R^A$ is optionally substituted alkyl, optionally substituted alkenyl, optionally substituted alkynyl, or optionally substituted carbocyclyl. In certain embodiments, $R^1$ is $-O$-isobutylenyl. In certain embodiments, $R^1$ is $-OR^A$, wherein $R^A$ is optionally substituted $C_{1-6}$ alkyl. In certain embodiments, $R^1$ is $-OR^A$, wherein $R^A$ is unsubstituted $C_{1-6}$ alkyl. In certain embodiments, $R^1$ is $-O$-propyl, $-O$-isopropyl, $-O$-isobutyl, or $-O$-isoamyl. In certain embodiments, $R^1$ is $-OR^A$, wherein $R^A$ is substituted $C_{1-6}$ alkyl. In certain embodiments, $R^1$ is $-O-C_{1-6}$alkyl-O-$C_{1-6}$alkyl. In certain embodiments, $R^1$ is $-OCH_2CH_2OCH_3$ or $-OCH_2CH_2CH_2OCH_3$. In certain embodiments, $R^1$ is $-O-C_{1-6}$alkyl-carbocyclyl. In certain embodiments, $R^1$ is $-O-CH_2$-cyclobutyl or $-O-CH_2$-cyclopropyl. In certain embodiments, $R^1$ is $-O-C_{1-6}$alkyl-heterocyclyl. In certain embodiments, $R^1$ is $-O-CH_2$-tetrahydropyranyl or $-O-CH_2$-oxetanyl. In certain embodiments, $R^1$ is $-OR^A$, wherein $R^A$ is optionally substituted heterocyclyl. In certain embodiments, $R^1$ is $-O$-tetrahydropyranyl or $-O$-oxetanyl. In certain embodiments, $R^1$ is $-OR^A$, wherein $R^A$ is optionally substituted aryl. In certain embodiments, $R^1$ is $-O$-phenyl. In certain embodiments, $R^1$ is $-OR^A$, wherein $R^A$ is optionally substituted heteroaryl.

In certain embodiments, $R^1$ is $R^y$, wherein $R^y$ is $-NR^BC(O)R^A$, $-NR^BSO_2R^A$, or $-(CR^zR^z)_nC(O)N(R^B)_2$; each $R^z$ is independently hydrogen or fluoro; and n is 0, 1, 2, 3, or 4. In certain embodiments, $R^1$ is $-NR^BC(O)R^A$. In certain embodiments, $R^1$ is $-NHC(O)R^A$. In certain embodiments, $R^1$ is $-NR^BSO_2R^A$. In certain embodiments, $R^1$ is $-NHSO_2R^A$. In certain embodiments, $R^1$ is $-(CR^zR^z)_nC(O)N(R^B)_2$. In certain embodiments, $R^1$ is $-CH_2C(O)N(R^B)_2$. In certain embodiments, each $R^z$ is hydrogen. In certain embodiments, n is 0. In certain embodiments, n is 1. In certain embodiments, n is 2. In certain embodiments, n is 3. In certain embodiments, n is 4.

As defined generally above, $R^2$ is hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$. In certain embodiments, $R^2$ is hydrogen. In some embodiments, $R^2$ is not hydrogen. In some embodiments, $R^2$ is halo. In certain embodiments, $R^2$ is fluoro. In certain embodiments, $R^2$ is chloro. In some embodiments, $R^2$ is optionally substituted alkyl, optionally substituted alkenyl, optionally substituted alkynyl, or optionally substituted carbocyclyl. In certain embodiments, $R^2$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^2$ is optionally substituted $C_{1-6}$ alkyl. In certain embodiments, $R^2$ is substituted $C_{1-6}$ alkyl. In certain embodiments, $R^2$ is —CF$_3$, CHF$_2$, or CH$_2$F. In certain embodiments, $R^2$ is —CF$_3$. In certain embodiments, $R^2$ is —CHF$_2$. In certain embodiments, $R^2$ is —C$_{1-6}$alkyl-carbocyclyl. In certain embodiments, $R^2$ is —CH$_2$-cyclopropyl or —CH$_2$-cyclobutyl. In certain embodiments, $R^2$ is unsubstituted $C_{1-6}$ alkyl. In certain embodiments, $R^2$ is methyl, ethyl, propyl, butyl, or pentyl. In certain embodiments, $R^2$ is isopropyl, isobutyl, or isoamyl. In certain embodiments, $R^2$ is isobutyl. In some embodiments, $R^2$ is —CN. In some embodiments, $R^2$ is optionally substituted carbocyclyl, optionally substituted aryl, optionally substituted heterocyclyl, or optionally substituted heteroaryl. In some embodiments, $R^2$ is —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$. In certain embodiments, $R^2$ is —N(R$^B$)$_2$. In certain embodiments, $R^2$ is —NHR$^B$. In certain embodiments, $R^2$ is —NH$_2$. In certain embodiments, $R^2$ is —OR$^A$. In certain embodiments, $R^2$ is —OH. In certain embodiments, $R^2$ is —OR$^A$, wherein R$^A$ is optionally substituted alkyl, optionally substituted alkenyl, optionally substituted alkynyl, or optionally substituted carbocyclyl. In certain embodiments, $R^2$ is —O-isobutylenyl. In certain embodiments, $R^2$ is —OR$^A$, wherein R$^A$ is optionally substituted $C_{1-6}$ alkyl. In certain embodiments, $R^2$ is —OR$^A$, wherein R$^A$ is unsubstituted $C_{1-6}$ alkyl. In certain embodiments, $R^2$ is —O-propyl, —O-isopropyl, —O-isobutyl, or —O-isoamyl. In certain embodiments, $R^2$ is —OCH(CH$_2$CH$_3$)$_2$. In certain embodiments, $R^2$ is —OCH(OH)CH(CH$_3$)$_2$. In certain embodiments, $R^2$ is —OR$^A$, wherein R$^A$ is substituted $C_{1-6}$ alkyl. In certain embodiments, $R^2$ is —O—C$_{1-6}$alkyl-O—C$_{1-6}$alkyl. In certain embodiments, $R^2$ is —OCH$_2$CH$_2$OCH$_3$, —OCH$_2$CH$_2$CH$_2$OCH$_3$, —OCH$_2$CH$_2$OH, or —OCH$_2$CH$_2$OCH$_2$CH$_2$CH$_3$. In certain embodiments, $R^2$ is —OCH$_2$CF$_3$ or —OCH$_2$CH$_2$CF$_3$. In certain embodiments, $R^2$ is —OCH(CH$_3$)$_2$, —OCH$_2$CH(CH$_3$)$_2$, —OCH$_2$CH$_2$CH$_3$, —OCH$_2$CH(CH$_3$)$_2$, —OCH$_2$CH$_2$CH$_2$OCH$_3$, or —OCH$_2$CH$_2$OCH$_3$. In certain embodiments, $R^2$ is —O—C$_{1-6}$alkyl-carbocyclyl. In certain embodiments, $R^2$ is —O—CH$_2$-cyclobutyl or —O—CH$_2$-cyclopropyl. In certain embodiments, $R^2$ is —O—CH$_2$-cyclopentyl or —O—CH$_2$CH$_2$-cyclohexyl. In certain embodiments, $R^2$ is —O—C$_{1-6}$alkyl-heterocyclyl. In certain embodiments, $R^2$ is —O—CH$_2$-tetrahydropyranyl or —O—CH$_2$-oxetanyl. In certain embodiments, $R^2$ is —O—C$_{1-6}$alkyl-aryl. In certain embodiments, $R^2$ is —O-benzyl or —OCH$_2$CH$_2$Ph. In certain embodiments, $R^2$ is —O—C$_{1-6}$ alkyl-heteroaryl. In certain embodiments, $R^2$ is —OR$^A$, wherein R$^A$ is optionally substituted heterocyclyl. In certain embodiments, $R^2$ is —O-tetrahydropyranyl or —O-oxetanyl. In certain embodiments, $R^2$ is —OR$^A$, wherein R$^A$ is optionally substituted aryl. In certain embodiments, $R^2$ is —O-phenyl. In certain embodiments, $R^2$ is —OR$^A$, wherein R$^A$ is optionally substituted heteroaryl. In certain embodiments, $R^2$ is —O-pyridyl. In certain embodiments, $R^2$ is —O-2-pyridyl. In certain embodiments, $R^2$ is —O-3-pyridyl. In certain embodiments, $R^2$ is —O-4-pyridyl. In certain embodiments, $R^2$ is —O-pyrimidinyl.

As defined generally above, $R^6$ is hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$. In certain embodiments, $R^6$ is not —CF$_3$ or —CHF$_2$. In certain embodiments, $R^6$ is hydrogen. In some embodiments, $R^6$ is not hydrogen. In some embodiments, $R^6$ is halo. In certain embodiments, $R^6$ is fluoro. In certain embodiments, $R^6$ is chloro. In some embodiments, $R^6$ is optionally substituted alkyl, optionally substituted alkenyl, optionally substituted alkynyl, or optionally substituted carbocyclyl. In certain embodiments, $R^6$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^6$ is optionally substituted $C_{1-6}$ alkyl. In certain embodiments, $R^6$ is substituted $C_{1-6}$ alkyl. In certain embodiments, $R^6$ is —C$_{1-6}$alkyl-carbocyclyl. In certain embodiments, $R^6$ is —CH$_2$-cyclopropyl or —CH$_2$-cyclobutyl. In certain embodiments, $R^6$ is unsubstituted $C_{1-6}$ alkyl. In certain embodiments, $R^6$ is methyl, ethyl, propyl, butyl, or pentyl. In certain embodiments, $R^6$ is isopropyl, isobutyl, or isoamyl. In certain embodiments, $R^6$ is isobutyl. In some embodiments, $R^6$ is —CN. In some embodiments, $R^6$ is optionally substituted carbocyclyl, optionally substituted aryl, optionally substituted heterocyclyl, or optionally substituted heteroaryl. In some embodiments, $R^6$ is —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$. In certain embodiments, $R^6$ is —N(R$^B$)$_2$. In certain embodiments, $R^6$ is —NHR$^B$. In certain embodiments, $R^6$ is —NH$_2$. In certain embodiments, $R^6$ is —OR$^A$. In certain embodiments, $R^6$ is —OH. In certain embodiments, $R^6$ is —OR$^A$, wherein $R^A$ is optionally substituted alkyl, optionally substituted alkenyl, optionally substituted alkynyl, or optionally substituted carbocyclyl. In certain embodiments, $R^6$ is —O— isobutylenyl. In certain embodiments, $R^6$ is —$OR^A$, wherein $R^A$ is optionally substituted $C_{1-6}$ alkyl. In certain embodiments, $R^6$ is —$OR^A$, wherein $R^A$ is unsubstituted $C_{1-6}$ alkyl. In certain embodiments, $R^6$ is —O-propyl, —O-isopropyl, —O-isobutyl, or —O-isoamyl. In certain embodiments, $R^6$ is —$OCH(CH_2CH_3)_2$. In certain embodiments, $R^6$ is —$OCH(OH)CH(CH_3)_2$. In certain embodiments, $R^6$ is —$OR^A$, wherein $R^A$ is substituted $C_{1-6}$ alkyl. In certain embodiments, $R^6$ is —O—$C_{1-6}$alkyl-O—$C_{1-6}$alkyl. In certain embodiments, $R^6$ is —$OCH_2CH_2OCH_3$, —$OCH_2CH_2CH_2OCH_3$, —$OCH_2CH_2OH$, or —$OCH_2CH_2OCH_2CH_2CH_3$. In certain embodiments, $R^6$ is —$OCH_2CF_3$ or —$OCH_2CH_2CH_2CF_3$. In certain embodiments, $R^6$ is —O—$C_{1-6}$alkyl-carbocyclyl. In certain embodiments, $R^6$ is —O—$CH_2$-cyclobutyl or —O—$CH_2$-cyclopropyl. In certain embodiments, $R^6$ is —O—$CH_2$-cyclopentyl or —O—$CH_2CH_2$-cyclohexyl. In certain embodiments, $R^6$ is —O—$C_{1-6}$alkyl-heterocyclyl. In certain embodiments, $R^6$ is —O—$CH_2$-tetrahydropyranyl or —O—$CH_2$-oxetanyl. In certain embodiments, $R^6$ is —O—$C_{1-6}$alkyl-aryl. In certain embodiments, $R^6$ is —O-benzyl or —$OCH_2CH_2Ph$. In certain embodiments, $R^6$ is —O—$C_{1-6}$alkyl-heteroaryl. In certain embodiments, $R^6$ is —$OR^A$, wherein $R^A$ is optionally substituted heterocyclyl. In certain embodiments, $R^6$ is —O-tetrahydropyranyl or —O-oxetanyl. In certain embodiments, $R^6$ is —$OR^A$, wherein $R^A$ is optionally substituted aryl. In certain embodiments, $R^6$ is —O-phenyl. In certain embodiments, $R^6$ is —$OR^A$, wherein $R^A$ is optionally substituted heteroaryl. In certain embodiments, $R^6$ is —O-pyridyl. In certain embodiments, $R^6$ is —O-2-pyridyl. In certain embodiments, $R^6$ is —O-3-pyridyl. In certain embodiments, $R^6$ is —O-4-pyridyl. In certain embodiments, $R^6$ is —O-pyrimidinyl.

As defined generally above, $R^7$ and $R^8$ are independently selected from the group consisting of hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(=O)$R^A$, —C(O)$OR^A$, —C(O)$SR^A$, —C(O)$N(R^B)_2$, —C(O)$N(R^B)N(R^B)_2$, —OC(O)$R^A$, —OC(O)$N(R^B)_2$, —$NR^BC(O)R^A$, —$NR^BC(O)N(R^B)_2$, —$NR^BC(O)N(R^B)N(R^B)_2$, —$NR^BC(O)OR^A$, —SC(O)$R^A$, —C(=$NR^B$)$R^A$, —C(=$NNR^B$)$R^A$, —C(=$NOR^A$)$R^A$, —C(=$NR^B$)$N(R^B)_2$, —$NR^BC(=NR^B)R^B$, —C(=S)$R^A$, —C(=S)$N(R^B)_2$, —$NR^BC(=S)R^A$, —S(O)$R^A$, —OS(O)$_2R^A$, —$SO_2R^A$, —$NR^BSO_2R^A$, and —$SO_2N(R^B)_2$. In some embodiments, at least one of $R^7$ and $R^8$ is not hydrogen. In some embodiments, $R^7$ is hydrogen and $R^8$ is not hydrogen. In some embodiments, $R^7$ is not hydrogen and $R^8$ is hydrogen. In some embodiments, $R^7$ and $R^8$ are not hydrogen.

In some embodiments, $R^7$ is hydrogen. In some embodiments, $R^7$ is halo. In some embodiments, $R^7$ is chloro. In some embodiments, $R^7$ is fluoro. In some embodiments, $R^7$ is —CN. In some embodiments, $R^7$ is optionally substituted $C_{1-6}$ alkyl. In some embodiments, $R^7$ is —$CF_3$ or —$CHF_2$. In some embodiments, $R^7$ is methyl or ethyl. In some embodiments, $R^7$ is isopropyl or isobutyl. In some embodiments, $R^7$ is —$OR^A$, —$N(R^B)_2$, —$SR^A$. In some embodiments, $R^7$ is —$OR^A$. In some embodiments, $R^7$ is —$OCH_3$. In some embodiments, $R^8$ is hydrogen. In some embodiments, $R^8$ is halo. In some embodiments, $R^8$ is chloro. In some embodiments, $R^8$ is fluoro. In some embodiments, $R^8$ is —CN. In some embodiments, $R^8$ is optionally substituted $C_{1-6}$ alkyl. In some embodiments, $R^8$ is —$CF_3$ or —$CHF_2$. In some embodiments, $R^8$ is methyl or ethyl. In some embodiments, $R^8$ is isopropyl or isobutyl. In some embodiments, $R^8$ is —$OR^A$, —$N(R^B)_2$, —$SR^A$. In some embodiments, R is —$OR^A$. In some embodiments, R is —$OCH_3$.

In some embodiments, $R^1$ and $R^2$ are taken together to form an optionally substituted carbocyclic, optionally substituted aryl, or optionally substituted heterocyclic ring. In some embodiments, $R^1$ and $R^2$ are taken together to form an optionally substituted carbocyclic ring. In some embodiments, $R^1$ and $R^2$ are taken together to form an optionally substituted aryl ring. In certain embodiments, $R^1$ and $R^2$ are taken together to form an optionally substituted benzene ring. In some embodiments, $R^1$ and $R^2$ are taken together to form an optionally substituted heterocyclic ring.

In some embodiments, $R^2$ and $R^8$ are taken together to form an optionally substituted carbocyclic, optionally substituted aryl, or optionally substituted heterocyclic ring. In some embodiments, $R^2$ and $R^8$ are taken together to form an optionally substituted carbocyclic ring. In some embodiments, $R^2$ and $R^8$ are taken together to form an optionally substituted aryl ring. In some embodiments, $R^2$ and $R^8$ are taken together to form an optionally substituted benzene ring. In some embodiments, $R^2$ and $R^8$ are taken together to form an optionally substituted heterocyclic ring.

In some embodiments, $R^6$ and $R^7$ are taken together to form an optionally substituted carbocyclic, optionally substituted aryl, or optionally substituted heterocyclic ring. In some embodiments, $R^6$ and $R^7$ are taken together to form an optionally substituted carbocyclic ring. In some embodiments, $R^6$ and $R^7$ are taken together to form an optionally substituted aryl ring. In some embodiments, $R^6$ and $R^7$ are taken together to form an optionally substituted benzene ring. In some embodiments, $R^6$ and $R^7$ are taken together to form an optionally substituted heterocyclic ring.

As defined generally above, $R^3$ is hydrogen, $C_{1-4}$ alkyl, or $C_{3-4}$ cycloalkyl. In certain embodiments, $R^3$ is hydrogen. In certain embodiments, $R^3$ is $C_{1-4}$ alkyl. In certain embodiments, $R^3$ is methyl. In certain embodiments, $R^3$ is ethyl. In certain embodiments, $R^3$ is propyl or butyl. In certain embodiments, $R^3$ is cyclopropyl. In certain embodiment, $R^3$ is cyclobutyl.

As defined generally above, $R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy, wherein Cy is optionally substituted $C_{3-7}$ cycloalkyl, optionally substituted 4- to 7-membered heterocyclyl, optionally substituted aryl, or optionally substituted heteroaryl. In certain embodiments, $R^4$ is hydrogen. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl, ethyl, or isopropyl. In certain embodiments, $R^4$ is substituted $C_{1-6}$ alkyl. In certain embodiments, $R^4$ is methoxyethyl. In certain embodiments, $R^4$ is hydroxyethyl or propane-1,2-diol. In certain embodiments, $R^4$ is optionally substituted $C_{3-7}$ cycloalkyl. In certain embodiments, $R^4$ is unsubstituted $C_{3-7}$ cycloalkyl. In certain embodiments, $R^4$ is cyclopropyl, cyclobutyl, cyclopentyl, or cyclohexyl. In certain embodiments, $R^4$ is optionally substituted 4- to 7-membered heterocyclyl. In certain embodiments, $R^4$ is optionally substituted 4- to 7-membered heterocyclyl having 1-2 heteroatoms independently selected from nitrogen, oxygen, and sulfur. In certain embodiments, $R^4$ is oxetane, tetrahydrofuran, or tetrahydropyran. In certain embodiments, $R^4$ is optionally substituted $C_{1-4}$ alkyl-Cy, wherein Cy is optionally substituted $C_{3-7}$ cycloalkyl, optionally substituted 4- to 7-membered heterocyclyl, optionally substituted aryl, or optionally substituted heteroaryl. In some embodiments, Cy is optionally substituted $C_{3-7}$ cycloalkyl. In some embodiments, Cy is optionally substituted 4- to 7-membered heterocyclyl having 1-2 heteroatoms independently selected from nitrogen, oxygen, and sulfur. In some embodiments, Cy is oxetane, tetrahydrofuran, or tetrahydropyran. In some embodiments, Cy is optionally substituted aryl. In some embodiments, Cy is optionally substituted phenyl. In some embodiments, Cy is unsubstituted phenyl. In some embodiments, Cy is optionally substituted heteroaryl having 1-3 heteroatoms independently selected from nitrogen, oxygen, and sulfur. In some embodiments, Cy is optionally substituted 5- to 6-membered heteroaryl having 1-3 heteroatoms independently selected from nitrogen, oxygen, and sulfur. In some embodiments, Cy is pyridyl. In some embodiments, $R^4$ is

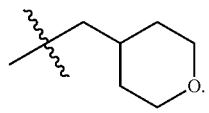

In some embodiments, $R^4$ is

In some embodiments, $R^4$ is

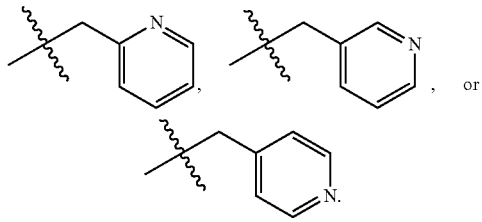

As defined generally above, $R^5$ is hydrogen, halo, —CN, optionally substituted $C_{1-4}$ alkyl, or optionally substituted $C_{3-4}$ cycloalkyl. In certain embodiments, $R^5$ is hydrogen. In certain embodiments, $R^5$ is halo. In certain embodiments, $R^5$ is chloro. In certain embodiments, $R^5$ is fluoro. In certain embodiments, $R^5$ is —CN. In certain embodiments, $R^5$ is optionally substituted $C_{1-4}$ alkyl. In certain embodiments, $R^5$ is unsubstituted $C_{1-4}$ alkyl. In certain embodiments, $R^5$ is methyl. In certain embodiments, $R^5$ is ethyl. In certain embodiments, $R^5$ is propyl or butyl. In certain embodiments, $R^5$ is $C_{1-4}$ alkyl substituted with one or more fluoro groups. In certain embodiments, $R^5$ is —$CF_3$. In certain embodiments, $R^5$ is —$CHF_2$. In certain embodiments, $R^5$ is optionally substituted $C_{3-4}$ cycloalkyl. In certain embodiments, $R^5$ is cyclopropyl or cyclobutyl.

As defined generally above, $R^x$ is optionally substituted $C_{1-4}$ alkyl or optionally substituted $C_{3-4}$ cycloalkyl. In certain embodiments, $R^x$ is optionally substituted $C_{1-4}$ alkyl. In certain embodiments, $R^x$ is unsubstituted $C_{1-4}$ alkyl. In certain embodiments, $R^x$ is methyl. In certain embodiments, $R^x$ is ethyl. In certain embodiments, $R^x$ is isopropyl. In certain embodiments, $R^x$ is propyl or butyl. In certain embodiments, $R^x$ is substituted $C_{1-4}$ alkyl. In certain embodiments, $R^x$ is $C_{1-4}$ alkyl substituted with hydroxyl or alkoxy. In certain embodiments, $R^x$ is hydroxyethyl or methoxyethyl. In certain embodiments, $R^x$ is optionally substituted $C_{3-4}$ cycloalkyl. In certain embodiments, $R^x$ is unsubstituted $C_{3-4}$ cycloalkyl. In certain embodiments, $R^x$ is cyclopropyl. In certain embodiments, $R^x$ is cyclobutyl.

As defined generally above, each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom. In some embodiments, $R^A$ is hydrogen. In some embodiments, $R^A$ is optionally substituted alkyl. In some embodiments, $R^A$ is optionally substituted alkyl substituted with a Cy group to form optionally substituted alkyl-Cy, wherein Cy is described herein. In some embodiments, $R^A$ is optionally substituted alkenyl or optionally substituted alkynyl. In some embodiments, $R^A$ is optionally substituted carbocyclyl, optionally substituted heterocyclyl, optionally substituted aryl, or optionally substituted heteroaryl. In some embodiments, $R^A$ is an oxygen protecting group when attached to an oxygen atom. In some embodiments, $R^A$ is not an oxygen protecting group. In some embodiments, $R^A$ is sulfur protecting group when attached to an sulfur atom. In some embodiments, $R^A$ is not a sulfur protecting group.

As defined generally above, each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, and a nitrogen protecting group, or two $R^B$ groups are taken together with their intervening atoms to form an optionally substituted heterocyclic ring. In some embodiments, $R^B$ is hydrogen. In some embodiments, $R^B$ is optionally substituted alkyl. In some embodiments, $R^B$ is optionally alkyl substituted with a Cy group to form optionally substituted alkyl-Cy, wherein Cy is described herein. In some embodiments, $R^B$ is optionally substituted alkenyl or optionally substituted alkynyl. In some embodiments, $R^B$ is optionally substituted carbocyclyl, optionally substituted heterocyclyl, optionally substituted aryl, or optionally substituted heteroaryl. In some embodiments, $R^B$ is a nitrogen protecting group. In some embodiments, $R^B$ is not a nitrogen protecting group. In some embodiments, two $R^B$ groups are taken together with their intervening atoms to form an optionally substituted heterocyclic ring.

In certain embodiments, a provided compound is a compound listed in Table 1, or a pharmaceutically acceptable salt thereof.

TABLE 1

| | Exemplary Compounds | |
|---|---|---|
| Cmpd No | Structure | LC-MS m/z (M + H) |
| 1 | | 331.2 |
| 2 | | |
| 3 | | |
| 4 | | |
| 5 | | |

TABLE 1-continued
Exemplary Compounds
| Cmpd No | Structure | LC-MS m/z (M + H) |
|---|---|---|
| 6 | 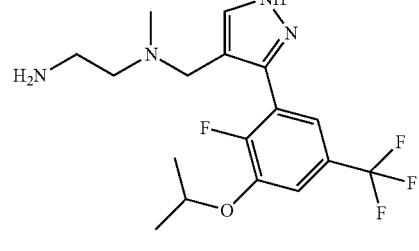 | |
| 7 | 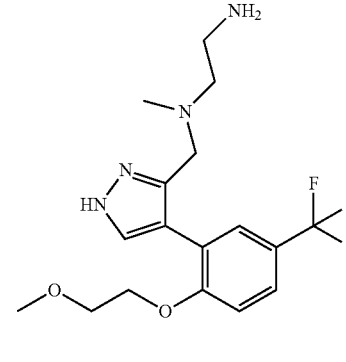 | |
| 8 | 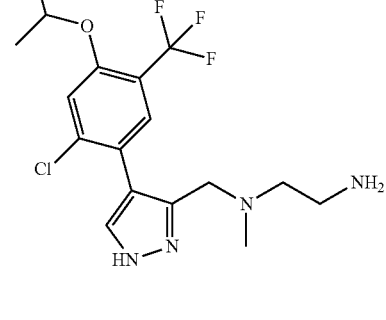 | |
| 9 | 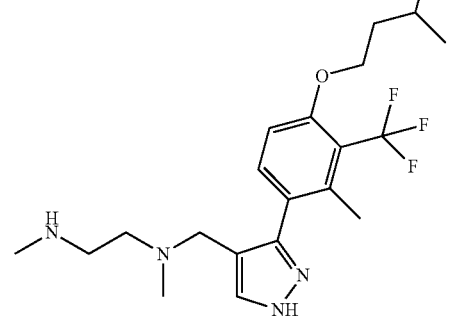 | |

TABLE 1-continued
Exemplary Compounds
| Cmpd No | Structure | LC-MS m/z (M + H) |
|---|---|---|
| 10 | 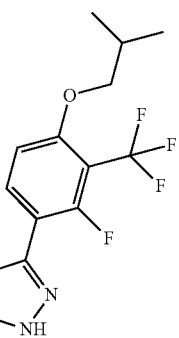 | |
| 11 | 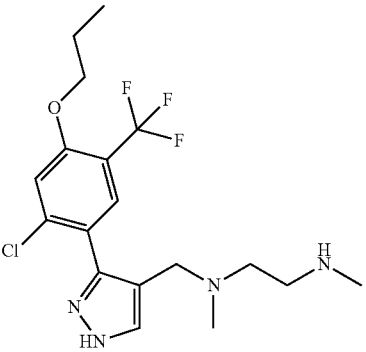 [SMILES: CCCOc1cc(Cl)c(-c2n[nH]cc2CN(C)CCNC)cc1C(F)(F)F] | |
| 12 | 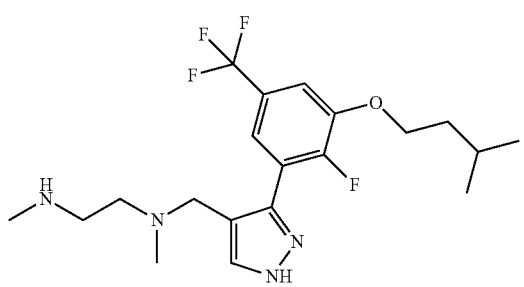 [SMILES: CNCCN(C)Cc1c[nH]nc1-c1cc(C(F)(F)F)cc(OCCC(C)C)c1F] | |
| 13 | 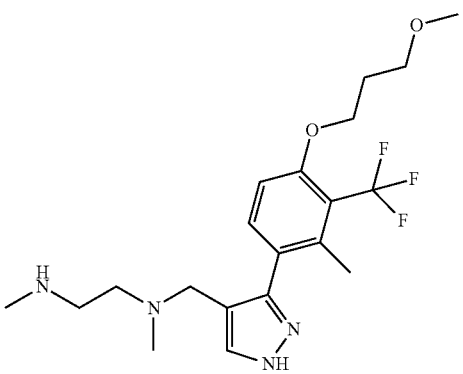 | |

TABLE 1-continued

| Exemplary Compounds | | |
|---|---|---|
| Cmpd No | Structure | LC-MS m/z (M + H) |
| 14 | | |
| 15 | | |
| 16 | | |
| 17 | | |

TABLE 1-continued

Exemplary Compounds

| Cmpd No | Structure | LC-MS m/z (M + H) |
|---|---|---|
| 18 | 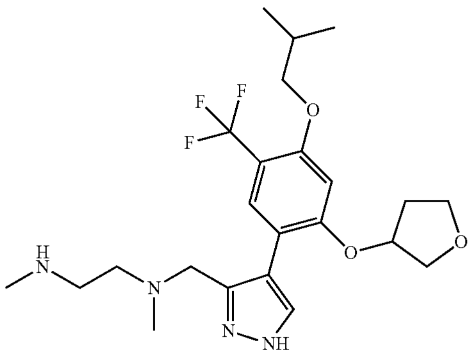 [SMILES: CNCCN(C)Cc1n[nH]cc1-c1cc(C(F)(F)F)c(OCC(C)C)cc1OC1CCOC1] | |
| 19 | 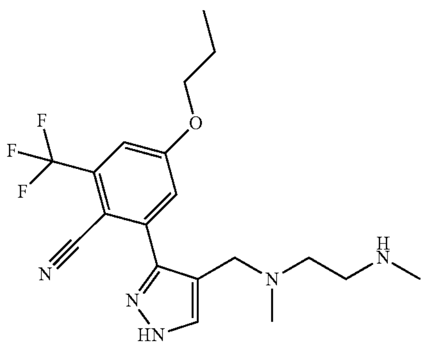 [SMILES: CCCOc1cc(-c2n[nH]cc2CN(C)CCNC)c(C#N)c(C(F)(F)F)c1] | |
| 20 | 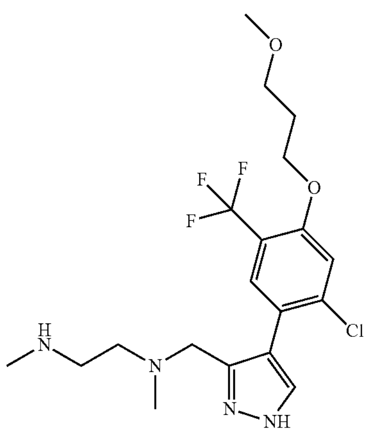 [SMILES: CNCCN(C)Cc1n[nH]cc1-c1cc(C(F)(F)F)c(OCCCOC)cc1Cl] | |
| 21 | 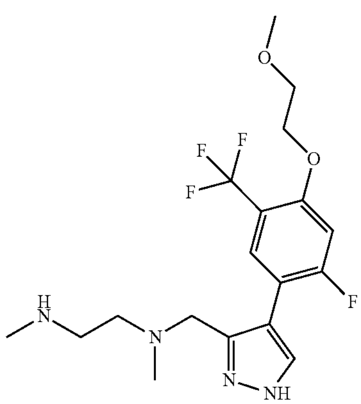 [SMILES: CNCCN(C)Cc1n[nH]cc1-c1cc(C(F)(F)F)c(OCCOC)cc1F] | |

TABLE 1-continued

Exemplary Compounds

| Cmpd No | Structure | LC-MS m/z (M + H) |
|---|---|---|
| 22 | 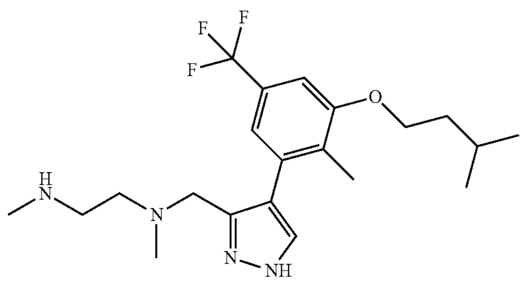 [SMILES: CNCCN(C)Cc1n[nH]cc1-c1cc(C(F)(F)F)cc(OCCC(C)C)c1C] | |
| 23 | 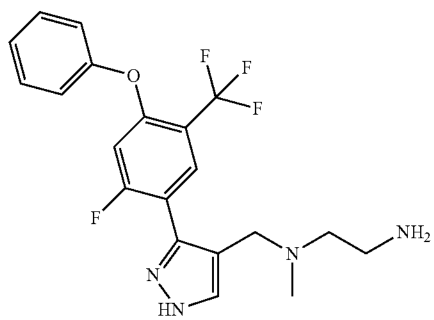 [SMILES: CN(CCN)Cc1c[nH]nc1-c1cc(C(F)(F)F)c(Oc2ccccc2)cc1F] | |
| 24 | 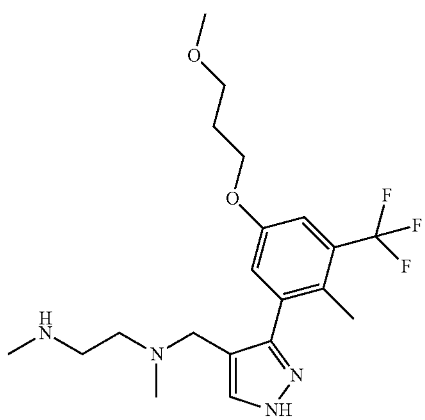 [SMILES: CNCCN(C)Cc1c[nH]nc1-c1cc(OCCCOC)cc(C(F)(F)F)c1C] | |
| 25 | 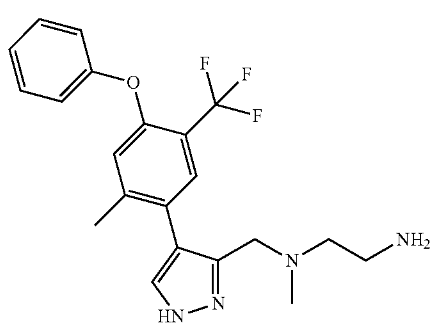 [SMILES: Cc1cc(Oc2ccccc2)c(C(F)(F)F)cc1-c1c[nH]nc1CN(C)CCN] | |

TABLE 1-continued

| Exemplary Compounds | | |
|---|---|---|
| Cmpd No | Structure | LC-MS m/z (M + H) |
| 26 | | |
| 27 | | |
| 28 | | |
| 29 | | |

49

TABLE 1-continued

Exemplary Compounds

| Cmpd No | Structure | LC-MS m/z (M + H) |
|---------|-----------|-------------------|
| 30 | 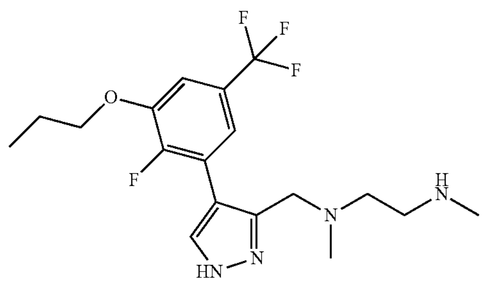 [SMILES: CCCOc1cc(C(F)(F)F)cc(-c2c[nH]nc2CN(C)CCNC)c1F] | |
| 31 | 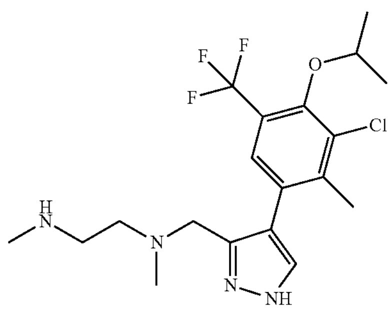 [SMILES: CNCCN(C)Cc1n[nH]cc1-c1cc(C(F)(F)F)c(OC(C)C)c(Cl)c1C] | |
| 32 | 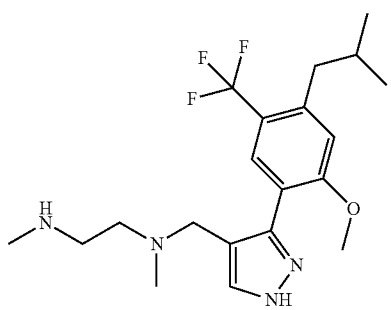 [SMILES: CNCCN(C)Cc1c[nH]nc1-c1cc(C(F)(F)F)c(CC(C)C)cc1OC] | |
| 33 | 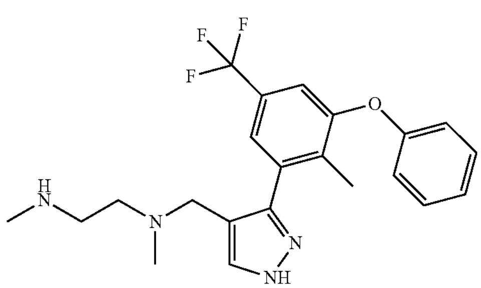 [SMILES: CNCCN(C)Cc1c[nH]nc1-c1cc(C(F)(F)F)cc(Oc2ccccc2)c1C] | |
| 34 | 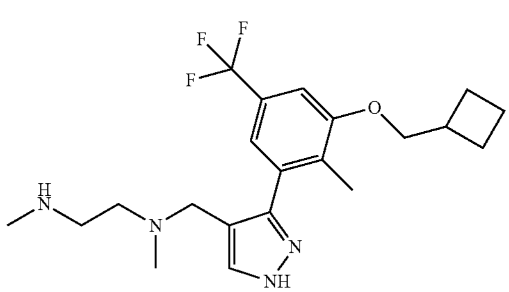 [SMILES: CNCCN(C)Cc1c[nH]nc1-c1cc(C(F)(F)F)cc(OCC2CCC2)c1C] | |

TABLE 1-continued

Exemplary Compounds

| Cmpd No | Structure | LC-MS m/z (M + H) |
|---|---|---|
| 35 | 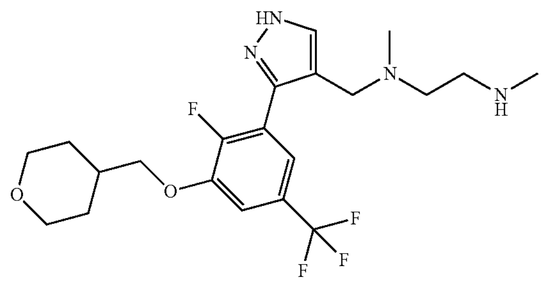 [SMILES: CNCCN(C)Cc1c[nH]nc1-c1cc(C(F)(F)F)cc(OCC2CCOCC2)c1F] | |
| 36 | 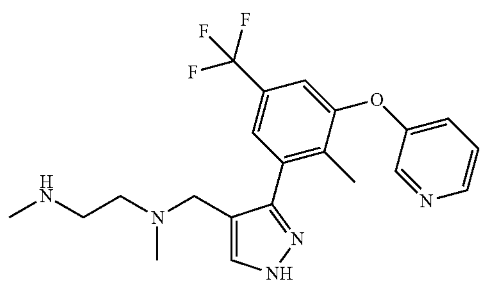 | |
| 37 | 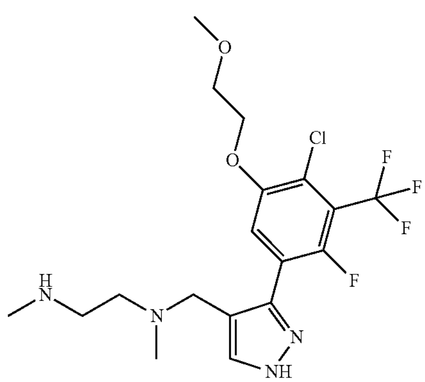 [SMILES: CNCCN(C)Cc1c[nH]nc1-c1cc(OCCOC)c(Cl)c(C(F)(F)F)c1F] | |
| 38 | 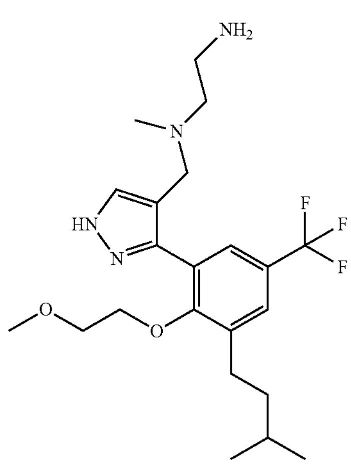 [SMILES: COCCOc1c(CCC(C)C)cc(C(F)(F)F)cc1-c1n[nH]cc1CN(C)CCN] | |

In certain embodiments, a provided compound inhibits PRMT1. In certain embodiments, a provided compound inhibits wild-type PRMT1. In certain embodiments, a provided compound inhibits a mutant PRMT1. In certain embodiments, a provided compound inhibits PRMT1, e.g., as measured in an assay described herein. In certain embodiments, the PRMT1 is from a human. In certain embodiments, a provided compound inhibits PRMT1 at an $IC_{50}$ less than or equal to 10 µM. In certain embodiments, a provided compound inhibits PRMT1 at an $IC_{50}$ less than or equal to 1 µM. In certain embodiments, a provided compound inhibits PRMT1 at an $IC_{50}$ less than or equal to 0.1 µM. In certain embodiments, a provided compound inhibits PRMT1 at an $IC_{50}$ less than or equal to 0.01 µM. In certain embodiments, a provided compound inhibits PRMT1 in a cell at an $EC_{30}$ less than or equal to 10 µM. In certain embodiments, a provided compound inhibits PRMT1 in a cell at an $EC_{30}$ less than or equal to 12 µM. In certain embodiments, a provided compound inhibits PRMT1 in a cell at an $EC_{30}$ less than or equal to 3 µM. In certain embodiments, a provided compound inhibits PRMT1 in a cell at an $EC_{30}$ less than or equal to 1 µM. In certain embodiments, a provided compound inhibits PRMT1 in a cell at an $EC_{30}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM. In some embodiments, a provided compound is selective for PRMT1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT1 relative to one or more other methyltransferases (e.g., all other methyltransferases).

It will be understood by one of ordinary skill in the art that the PRMT1 can be wild-type PRMT1, or any mutant or variant of PRMT1.

The present disclosure provides pharmaceutical compositions comprising a compound described herein, e.g., a compound of Formula (I-a) or (I-b), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting PRMT1. In certain embodiments, the effective amount is an amount effective for treating a PRMT1-mediated disorder. In certain embodiments, the effective amount is a prophylactically effective amount. In certain embodiments, the effective amount is an amount effective to prevent a PRMT1-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

In some embodiments, a pharmaceutical composition described herein is sterilized.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I-a) or (I-b). In certain embodiments, the additional therapeutically active agent is not a compound of Formula (I-a) or (I-b). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, an additional therapeutically active agent is prednisolone, dexamethasone, doxorubicin, vincristine, mafosfamide, cisplatin, carboplatin, Ara-C, rituximab, azacitadine, panobinostat, vorinostat, everolimus, rapamycin, ATRA (all-trans retinoic acid), daunorubicin, decitabine, Vidaza, mitoxantrone, or IBET-151.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of PRMT1. In some embodiments, methods of treating PRMT1-mediated disorder in a subject are provided which comprise administering an effective amount of a compound described herein (e.g., a compound of Formula (I-a) or (I-b)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a PRMT1-mediated disorder. In certain embodiments, the subject is susceptible to a PRMT1-mediated disorder.

As used herein, the term "PRMT1-mediated disorder" means any disease, disorder, or other pathological condition in which PRMT1 is known to play a role. Accordingly, in some embodiments, the present disclosure relates to treating or lessening the severity of one or more diseases in which PRMT1 is known to play a role.

In some embodiments, the present disclosure provides a method of inhibiting PRMT1 comprising contacting PRMT1 with an effective amount of a compound described herein (e.g., a compound of Formula (I-a) or (I-b)), or a pharmaceutically acceptable salt thereof. The PRMT1 may be purified or crude, and may be present in a cell, tissue, or subject. Thus, such methods encompass both inhibition of in vitro and in vivo PRMT1 activity. In certain embodiments, the method is an in vitro method, e.g., such as an assay method. It will be understood by one of ordinary skill in the art that inhibition of PRMT1 does not necessarily require that all of the PRMT1 be occupied by an inhibitor at once. Exemplary levels of inhibition of PRMT1 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting PRMT1 activity in a subject in need thereof (e.g., a subject diagnosed as having a PRMT1-mediated disorder) comprising administering to the subject an effective amount of a compound described herein (e.g., a compound of Formula (I-a) or (I-b)), or a pharmaceutically acceptable salt thereof, or a pharmaceutical composition thereof.

In certain embodiments, provided is a method of modulating gene expression in a cell which comprises contacting a cell with an effective amount of a compound of Formula (I-a) or (I-b), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I-a) or (I-b), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, a method is provided of selecting a therapy for a subject having a disease associated with PRMT1-mediated disorder or mutation comprising the steps of determining the presence of PRMT1-mediated disorder or gene mutation in the PRMT1 gene or and selecting, based on the presence of PRMT1-mediated disorder a gene mutation in the PRMT1 gene a therapy that includes the administration of a provided compound. In certain embodiments, the disease is cancer.

In certain embodiments, a method of treatment is provided for a subject in need thereof comprising the steps of determining the presence of PRMT1-mediated disorder or a gene mutation in the PRMT1 gene and treating the subject in need thereof, based on the presence of a PRMT1-mediated disorder or gene mutation in the PRMT1 gene with a therapy that includes the administration of a provided compound. In certain embodiments, the subject is a cancer patient. In some embodiments, a compound provided herein is useful in treating a proliferative disorder, such as cancer. For example, while not being bound to any particular mechanism, protein arginine methylation by PRMT1 is a modification that has been implicated in signal transduction, gene transcription, DNA repair and mRNA splicing, among others; and overexpression of PRMT1 within these pathways is often associated with various cancers. Thus, compounds which inhibit the action of PRMT1, as provided herein, are effective in the treatment of cancer.

In some embodiments, compounds provided herein are effective in treating cancer through the inhibition of PRMT1. For example, PRMT1 overexpression has been observed in various human cancers, including, but not limited to, breast cancer, prostate cancer, lung cancer, colon cancer, bladder cancer, and leukemia. In one example, PRMT1 specifically deposits an asymmetric dimethylarginine (aDMA) mark on histone H4 at arginine 3 (H4R3me2a), and this mark is associated with transcription activation. In prostate cancer, the methylation status of H4R3 positively correlates with increasing tumor grade and can be used to predict the risk of prostate cancer recurrence (Seligson et al., *Nature* 2005 435, 1262-1266). Thus, in some embodiments, inhibitors of PRMT1, as described herein, are useful in treating cancers associated with the methylation status of H4R3, e.g., prostate cancer. Additionally, the methylarginine effector molecule TDRD3 interacts with the H4R3me2a mark, and overexpression of TDRD3 is linked to poor prognosis for the survival of patients with breast cancer (Nagahata et al., *Cancer Sci.* 2004 95, 218-225). Thus, in some embodiments, inhibitors of PRMT1, as described herein, are useful in treating cancers associated with overexpression of TDRD3, e.g., breast cancer, as inhibition of PRMT1 leads to a decrease in methylation of H4R3, thereby preventing the association of overexpressed TDRD3 with H4R3me2a. In other examples, PRMT1 is known to have non-histone substrates. For example, PRMT1, when localized to the cytoplasm, methylates proteins that are involved in signal transduction pathways, e.g., the estrogen receptor (ER). The expression status of ER in breast cancer is critical for prognosis of the disease, and both genomic and non-genomic ER pathways have been implicated in the pathogenesis of breast cancer. For example, it has been shown that PRMT1 methylates ERα, and that ERα methylation is required for the assembly of ERα with SRC (a proto-oncogene tyrosine-protein kinase) and focal adhesion kinase (FAK). Further, the silencing of endogenous PRMT1 resulted in the inability of estrogen to activate AKT. These results suggested that PRMT1-mediated ERα methylation is required for the activation of the SRC-PI3K-FAK cascade and AKT, coordinating cell proliferation and survival. Thus, hypermethylation of ERα in breast cancer is thought to cause hyperactivation of this signaling pathway, providing a selective survival advantage to tumor cells (Le Romancer et al., *Mol. Cell* 2008 31, 212-221; Le Romancer et al., *Steroids* 2010 75, 560-564). Accordingly, in some embodiments, inhibitors of PRMT1, as described herein, are useful in treating cancers associated with ERα methylation, e.g., breast cancer. In yet another example, PRMT1 has been shown to be involved in the regulation of leukemia development. For example, SRC-associated in mitosis 68 kDa protein (SAM68; also known as KHDRBS1) is a well-characterized PRMT1 substrate, and when either SAM68 or PRMT1 is fused directly to the myeloid/lymphoid leukemia (MLL) gene, these fusion proteins can activate MLL oncogenic properties, implying that the methylation of SAM68 by PRMT1 is a critical signal for the development of leukemia (Cheung et al., *Nature Cell Biol.* 2007 9, 1208-1215). Accordingly, in some embodiments, inhibitors of PRMT1, as described herein, are useful in treating cancers associated with SAM68 methylation, e.g., leukemia. In still another example, PRMT1 is implicated in leukemia development through its interaction with AE9a, a splice isoform of AML1-ETO (Shia et al., *Blood* 2012 119:4953-62). Knockdown of PRMT1 affects expression of certain AE9a-activated genes and suppresses AE9a's self-renewal capability. It has also been shown that AE9a recruits PRMT1 to AE9a activated gene promoters, which leads to increased H4 Arg3 methylation, H3 Lys9/14 acetylation, and transcription activated. Accordingly, in some embodiments, inhibitors of PRMT1, as described herein, are useful in treating cancers associated with AML1-ETO, e.g., leukemia. Thus, without being bound by any particular mechanism, the inhibition of PRMT1, e.g., by compounds described herein, is beneficial in the treatment of cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., "Waldenstrim's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomal-leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a compound provided herein is useful in treating diseases associated with increased levels of circulating asymmetric dimethylarginine (aDMA), e.g., cardiovascular disease, diabetes, kidney failure, renal disease, pulmonary disease, etc. Circulating aDMA is produced by the proteolysis of asymmetrically dimethylated proteins. PRMT1 mediates aDMA methylation. aDMA levels are directly involved in various diseases as aDMA is an endogenous competitive inhibitor of nitric oxide synthase (NOS), thereby reducing the production of nitric oxide (NO) (Vallance et al., *J. Cardiovasc. Pharmacol.* 1992 20(Suppl. 12):S60-2). NO functions as a potent vasodilator in endothelial vessels, and as such inhibiting its production has major consequences on the cardiovascular system. For example, since PRMT1 is a major enzyme that generates aDMA, the dysregulation of its activity is likely to regulate cardiovascular diseases (Boger et al., *Ann. Med.* 2006 38:126-36), and other pathophysiological conditions such as diabetes mellitus (Sydow et al., *Vasc. Med.* 2005 10(Suppl. 1):S35-43), kidney failure (Vallance et al., *Lancet* 1992 339:572-5), and chronic pulmonary diseases (Zakrzewicz et al., *BMC Pulm. Med.* 2009 9:5). Additionally, it has been demonstrated that the expression of PRMT1 is increased in coronary heart disease (Chen et al., *Basic Res. Cardiol.* 2006 101:346-53). In another example, aDMA elevation is seen in patients with renal failure, due to impaired clearance of this metabolite from the circulation (Jacobi et al., *Am. J. Nephrol.* 2008 28:224-37). Thus, circulating aDMA levels is observed in many pathophysiological situations. Accordingly, without being bound by any particular mechanism, the inhibition of PRMT1, e.g., by compounds described herein, results in the decrease of circulating aDMA, which is beneficial in the treatment of diseases associated with increased levels of circulating aDMA, e.g., cardiovascular disease, diabetes, kidney failure, renal disease, pulmonary disease, etc. In certain embodiments, a compound described herein is useful for treating vascular diseases.

In some embodiments, a compound provided herein is useful in treating metabolic disorders. For example, PRMT1 has been shown to enhance mRNA levels of FoxO1 target genes in gluconeogenesis, which results in increased hepatic glucose production, and knockdown of PRMT1 promotes inhibition of FoxO1 activity and thus inhibition of hepatic gluconeogenesis (Choi et al., *Hepatology* 2012 56:1546-56). Additionally, genetic haploinsufficiency of Prmt1 has been shown to reduce blood glucose levels in mouse models. Thus, without being bound by any particular mechanism, the inhibition of PRMT1, e.g., by compounds described herein, is beneficial in the treating of metabolic disorders, such as diabetes. In some embodiments, a provided compound is useful in treating type I diabetes. In some embodiments, a provided compound is useful in treating type II diabetes.

In some embodiments, a compound provided herein is useful in treating muscular dystrophies. For example, PRMT1 methylates the nuclear poly(A)-binding protein (PABPN1) in a region located near its C-terminus (Perreault et al., *J. Biol. Chem.* 2007 282:7552-62). This domain is involved in the aggregation of the PABPN1 protein, and abnormal aggregation of this protein is involved in the disease oculopharyngeal muscular dystrophy (Davies et al., *Int. J. Biochem. Cell. Biol.* 2006 38:1457-62). Thus, without being bound by any particular mechanism, the inhibition of PRMT1, e.g., by compounds described herein, is beneficial in the treatment of muscular dystrophies, e.g., oculopharyngeal muscular dystrophy, by decreasing the amount of methylation of PABPN1, thereby decreasing the amount of PABPN1 aggregation.

In some embodiments, a compound provided herein is useful in treating autoimmune disease. For example, several lines of evidence strongly suggest that PRMT1 inhibitors may be valuable for the treatment of autoimmune diseases, e.g., rheumatoid arthritis. PRMT1 is known to modify and regulate several critical immunomodulatory proteins. For example, post-translational modifications (e.g., arginine methylation), within T cell receptor signaling cascades allow T lymphocytes to initiate a rapid and appropriate immune response to pathogens. Co-engagement of the CD28 costimulatory receptor with the T cell receptor elevates PRMT1 activity and cellular protein arginine methylation, including methylation of the guanine nucleotide exchange factor Vav1 (Blanchet et al., *J. Exp. Med.* 2005 202:371-377). PRMT1 inhibitors are thus expected to diminish methylation of the guanine exchange factor Vav1, resulting in diminished IL-2 production. PRMT1 is known to enhance NFkB p65-driven transcription and facilitate the transcription of p65 target genes like TNFα (Covic et al., *Embo. J.* 2005 24:85-96). Thus, in some embodiments, PRMT1 inhibitors, e.g., those described herein, are useful in treating autoimmune disease by decreasing the transcription of p65 target genes like TNFα. These examples demonstrate an important role for arginine methylation by PRMT1 in inflammation. Thus, without being bound by any particular mechanism, the inhibition of PRMT1, e.g., by compounds described herein, is beneficial in the treatment of autoimmune diseases.

In some embodiments, a compound provided herein is useful in treating neurological disorders, such as amyotrophic lateral sclerosis (ALS). For example, a gene involved in ALS, TLS/FUS, often contains mutated arginines in certain familial forms of this disease (Kwiatkowski et al., *Science* 2009 323:1205-8). These mutants are retained in the cytoplasm, which is similar to reports documenting the role arginine methylation plays in nuclear-cytoplasmic shuffling (Shen et al., *Genes Dev.* 1998 12:679-91). This implicates PRMT1 function in this disease, as it was demonstrated that TLS/FUS is methylated on at least 20 arginine residues (Rappsilber et al., *Anal. Chem.* 2003 75:3107-14). Thus, in some embodiments, the inhibition of PRMT1, e.g., by compounds provided herein, are useful in treating ALS by decreasing the amount of TLS/FUS arginine methylation Scheme 1

Scheme 1 shows a general synthesis route to pyrazole compounds of formula I-a, wherein $R^{1'}$ and $R^{2'}$ are either the same as $R^1$ and $R^2$ or are substituents which serve as precursors for synthetic conversion to $R^1$ and $R^2$ wherein, $R^1$, $R^2$, $R^G$, $R^7$, $R^8$, $R^3$, $R^x$, X, Y and Z and are as defined above. In the first step iodopyrazole carboxaldehydes of general formula XI are allowed to react with mono-Boc protected ethylenediamines XII under reductive amination conditions (e.g. sodium cyanoborohydride and catalytic acid such as acetic acid) in an appropriate solvent such as methanol to give intermediates of general formula XIII.

Suzuki reaction of the latter with boronic acids or boronic esters of general formula XIV in the presence of a palladium catalyst (e.g. PdCl$_2$(dppf)) and a base (e.g. potassium carbonate) in an organic solvent (e.g. toluene) at elevated temperature yields intermediates of general formula XV. In a subsequent optional step or steps, either $R^{1'}$ or $R^{2'}$ or both $R^{1'}$ and $R^{2'}$ may be converted to yield $R^1$ and $R^2$ substituents present in certain embodiments of final compounds of formula I. For example compounds wherein $R^2$ is an alkoxy group can be synthesized by alkylating intermediates of formula XV where $R^{2'}$ is OH with a suitable alkylbromide or iodide using an appropriate base (e.g. potassium carbonate) in a suitable organic solvent (e.g. tetrahydrofuran) at room or elevated temperature. In a final deprotection step the N-Boc protecting of XV can be removed under a variety of conditions, for example using an acid (e.g. HCl, TFA), in a suitable organic solvent (e.g. ethanol, THF, dichloromethane) to give compounds of formula I.

In certain embodiments, iodopyrazole carboxaldehydes of general formula XI are prepared from suitable known pyrazole compound intermediates by established synthetic chemistry methods. Standard methods include direct iodination of a pyrazole 3-carboxylate and Sandmeyer reaction of a 3-amino pyrazole 4-carboxylate. In certain embodiments, iodopyrazole carboxaldehydes are derived from iodopyrazole carboxylates by reduction to a hydroxymethyl group followed by oxidation to carboxaldehyde. The mono-Boc protected ethylenediamines XII can be synthesized by standard methods known in the literature for derivatizing or preparing ethylenediamines. For example intermediates of formula XII may be prepared by treatment of the corresponding unprotected diamine precursorswith Boc$_2$O and purifying the mixture of mono and dibocylated products. In certain embodiments, phenyl boronic acids or esters of general formula XIV are either commercially available or can be prepared by standard method for example by boronylation of the corresponding commercially available phenylbromides.

In certain embodiments, pyrazole compounds of general formula II-a can be prepared from iodopyrazole carboxaldehydes of general formula XXI as depicted in Scheme 2. In certain embodiments where $R^4$ is hydrogen compounds of general formula II-a are equivalent to compounds of general formula III-a which are tautomers. In certain embodiments $R^{4'}$ is a protecting group such as tetrahydropyranyl (THP) which maybe cleaved to hydrogen under acidic conditions in the final Boc-deprotection step. In certain embodiments, iodopyrazole carboxaldehydes of general formula XXI can be prepared as depicted in Scheme 3.

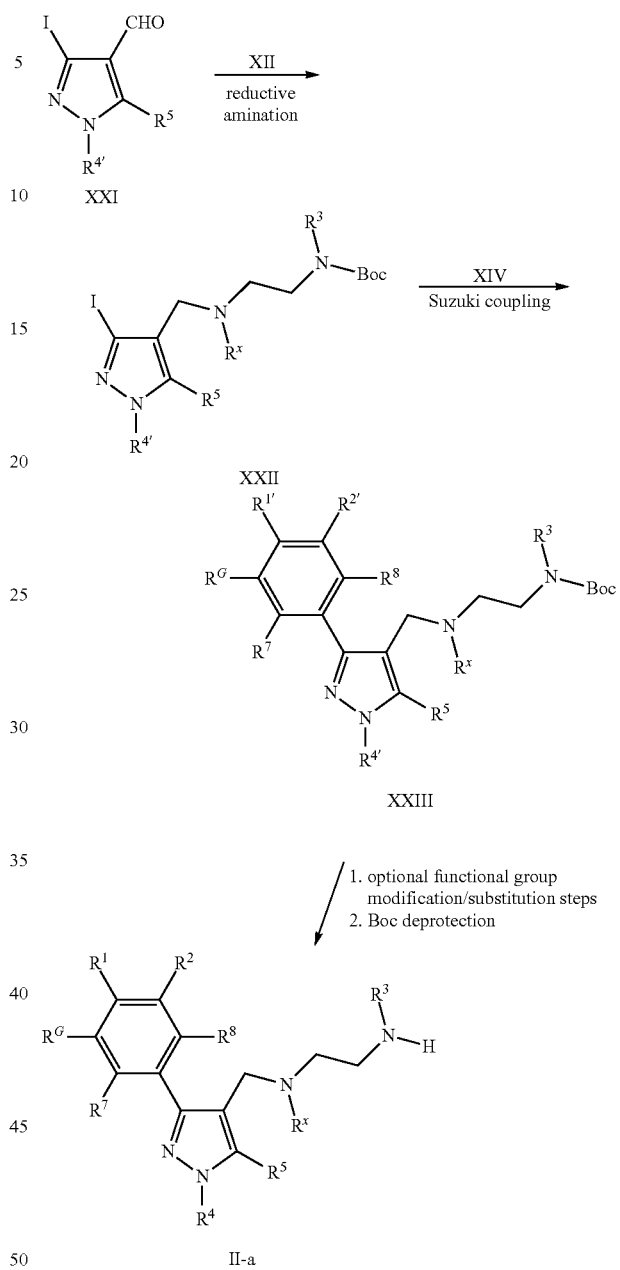

Scheme 2

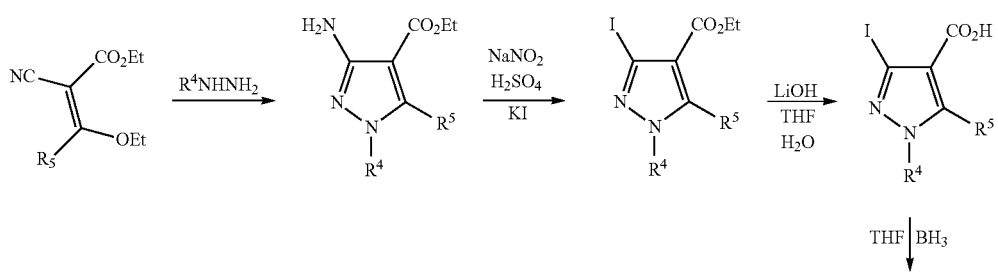

Scheme 3

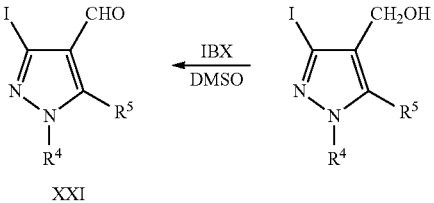

In certain embodiments, iodopyrazole carboxaldehydes of general formula XXI can be prepared as depicted in Scheme 4 which also provides iodopyrazole carboxyaldehydes of general formula XXXI. Thus, alkylation of intermediates of general formula XXX gives a mixture of pyrazole nitrogen alkylated isomers which are separated by chromatography to give pure isomers XXI and XXXI. In certain embodiments, pyrazole compounds of general formula III-a can be prepared from iodopyrazole carboxaldehydes of general formula XXXI as depicted in Scheme 5.

Scheme 4

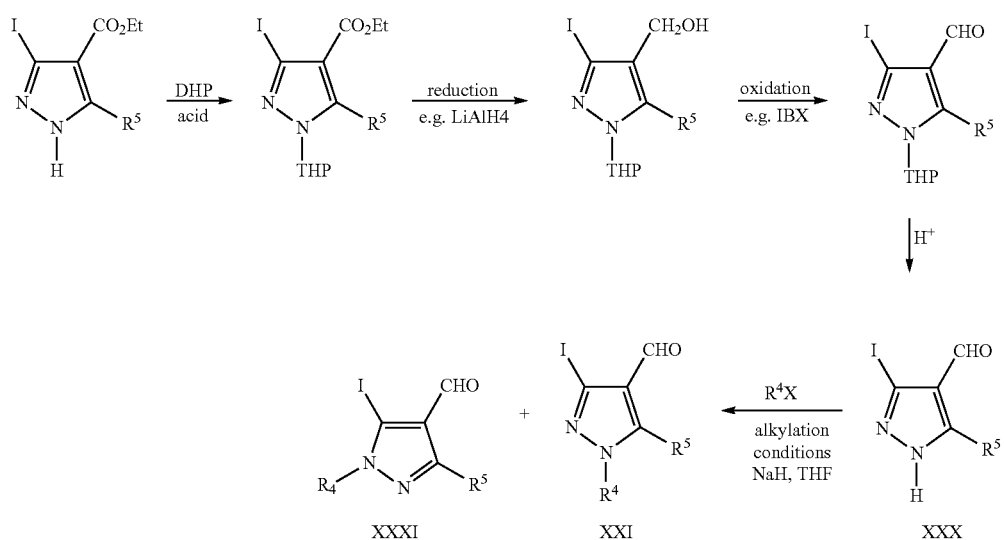

Scheme 5

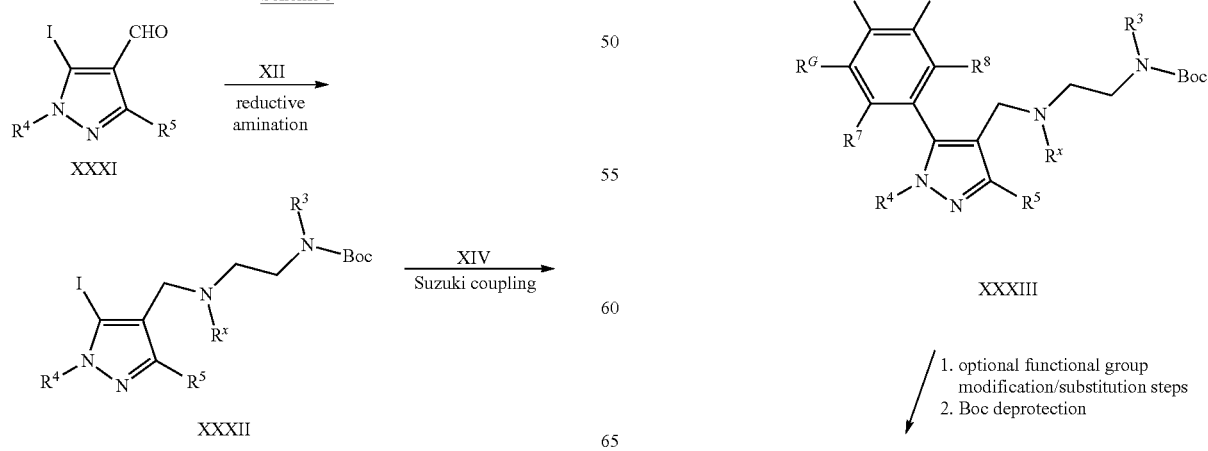

1. optional functional group modification/substitution steps
2. Boc deprotection

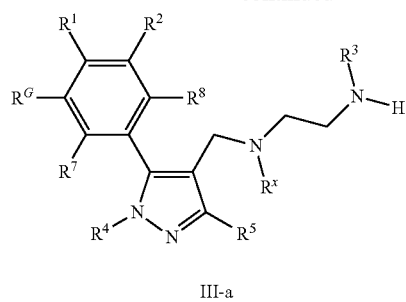

III-a

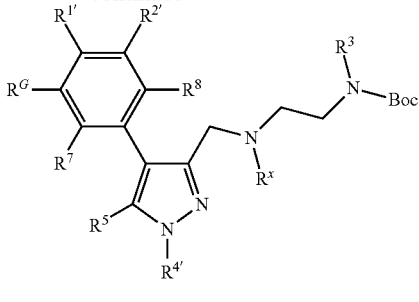

XLIII

In certain embodiments, pyrazole compounds of general formula IV-a are prepared from iodopyrazole carboxaldehydes of general formula XLI as depicted in Scheme 6. In certain embodiments where $R^4$ is hydrogen compounds of general formula IV-a are equivalent to compounds of general formula V-a which are tautomers. In certain embodiments where $R^4$ in compounds of formula IV-a is hydrogen, $R^{4'}$ in intermediate XLI may be a selected protecting group such as tetrahydropyranyl (THP) which can be cleaved to hydrogen under acidic conditions in the final Boc-deprotection step.

1. optional functional group modification/substitution steps
2. Boc deprotection Scheme 6

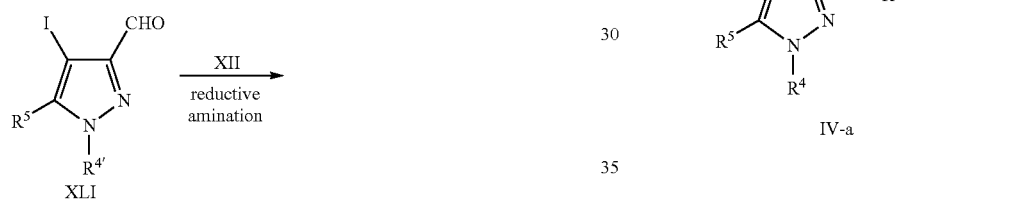

IV-a

In certain embodiments, iodopyrazole carboxaldehydes of general formula XLI and LI can be prepared as depicted in Scheme 7. In certain embodiments an $R^4$ group of iodopyrazole carboxaldehydes maybe introduced by alkylation of intermediates of formula XLVII. This reaction can give a mixture of intermediate compounds of formulas XLI and LI which may be separated by chromatography. The THP protected intermediates of formula XLVI can be used to prepare compounds of formula IV-a where $R^4$=H as also depicted in Scheme 7.

Scheme 7

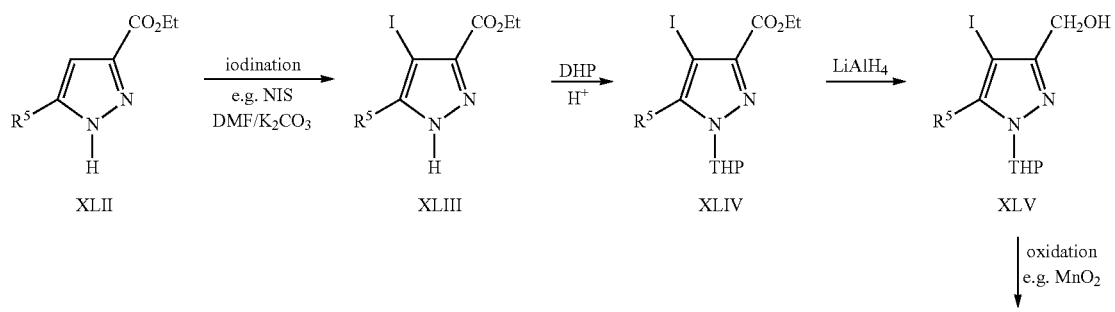

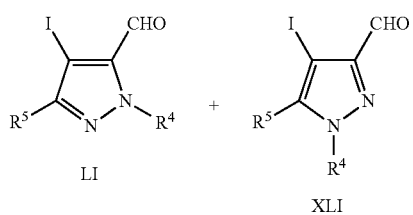
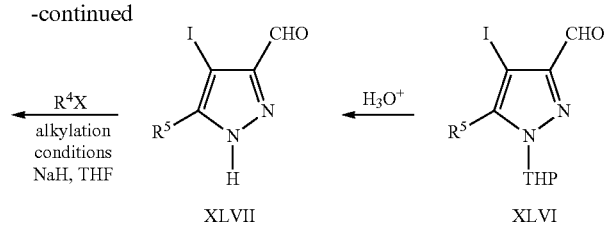

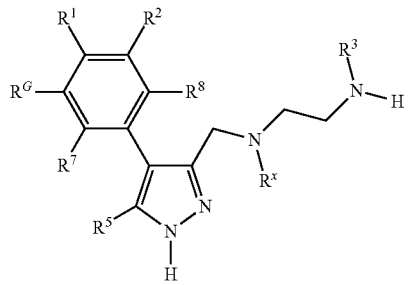

IV-a = V-a (R⁴ is H)

In certain embodiments, pyrazole compounds of general formula V-a can be prepared from iodopyrazole carboxaldehydes of general formula LI as depicted in Scheme 8.

Scheme 8

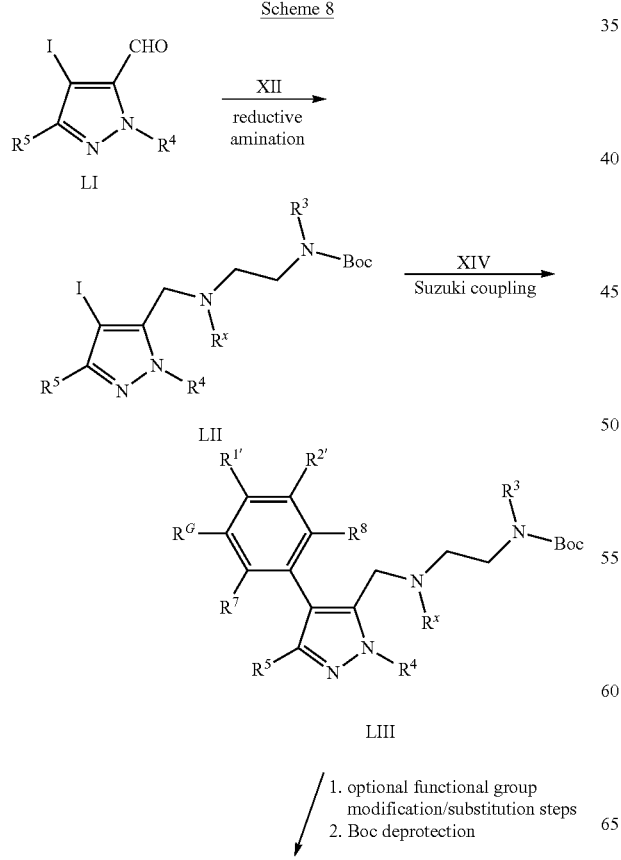

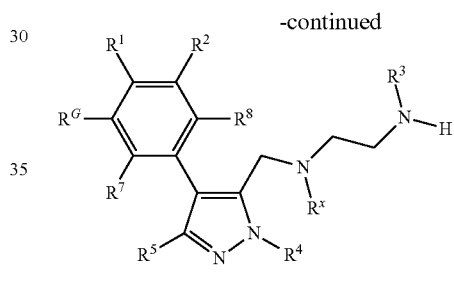

V-a

In certain embodiments, phenyl boronic acids or esters of general formula XIV are commercially available or can be prepared from commercially available or known corresponding phenyl bromide precursors of general formula LX by standard methods. One such method to prepare pinacol boranes XIVd is depicted in Scheme 9.

Scheme 9

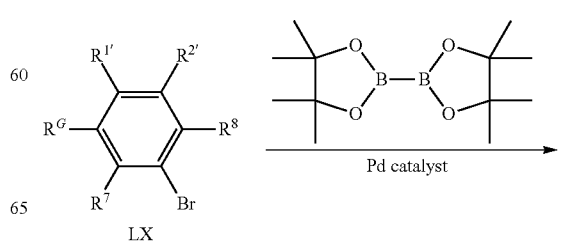

-continued

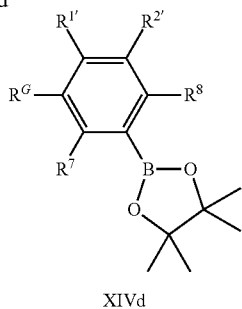

XIVd

In certain embodiments, compounds of formula XIV are prepared by multistep organic synthesis using known methods. For example bromides LX may be prepared from corresponding aniline intermediate compounds by Sandmeyer reaction. The required aniline intermediates can in turn be prepared from the corresponding nitrobenzenes by reduction of the nitro group under standard conditions (e.g. $Pd/H_2$, $SnCl_2$, Fe/HOAc).

In certain embodiments, pyrazole compounds of general formulas I-b, IIb, IIIb, IV-b and V-b can be prepared using the same general methods described above for compounds of general formulas I-a, II-a, III-a, IV-a and V-a by use of an $R^{y\prime}$ or $R^y$ group in place of the $R^1$ or $R^{1\prime}$ groups in the respective formulas.

EXAMPLES

In order that the invention described herein may be more fully understood, the following examples are set forth. It should be understood that these examples are for illustrative purposes only and are not to be construed as limiting this invention in any manner.

Synthetic Methods

General methods and experimental procedures for preparing and characterizing compounds of the present invention are set forth below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator. Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (e.g., including, but not limited to the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC). Exemplified compounds were dissolved in either MeOH or MeCN to a concentration of approximately 1 mg/mL and analyzed by injection of 0.5-10 μL into an appropriate LCMS system using the methods provided in the following table:

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| A | Shim-pack XR-ODS 2.2 μm 3.0 × 50 mm | Water/0.05% TFA | ACN/0.05% TFA | 1 | 5% to 100% B in 2.0 minutes, 100% B for 1.1 minutes, 100% to 5% B in 0.2 minutes, then stop | 250 | 1.5 |
| B | Gemini-NX 3 μm C18 110A | Water/0.04% Ammonia | ACN | 1 | 5% to 100% B in 2.0 minutes, 100% B for 1.1 minutes, 100% to 5% B in 0.1 minutes, then stop | 200 | 0.75 |
| C | Shim-pack XR-ODS 1.6 μm 2.0 × 50 mm | Water/0.05% FA | ACN/0.05% FA | 1 | 5% to 100% B in 2.0 minutes, 100% B for 1.1 minutes, 100% to 5% B in 0.1 minutes, then stop | 250 | 0.85 |
| D | Shim-pack XR-ODS 2.2 μm 3.0 × 50 mm | Water/0.05% TFA | ACN/0.05% TFA | 1 | 5% to 100% B in 2.0 minutes, 100% B for 1.1 minutes, 100% to 5% B in 0.1 minutes, then stop | 250 | 0.95 |
| E | Waters Xselect C18 3.5 μm 3.0 × 50 mm | Water/0.05% FA | ACN/0.05% FA | 0.9 | 5% to 100% B in 2.0 minutes, 100% B for 1.2 minutes, 100% to 5% B in 0.1 minutes, then stop | 250 | 1.5 |
| F | Shim-pack XR-ODS 2.2 μm 3.0 × 50 mm | Water/0.05% TFA | ACN/0.05% TFA | 1 | 5% to 80% B in 3.25 minutes, 80% B for 1.35 minutes, 80% to 5% B in 0.3 minutes, then stop | 200 | 0.95 |
| G | Shim-pack XR-ODS 2.2 μm 3.0 × 50 mm | Water/0.05% TFA | ACN/0.05% TFA | 1 | 5% to 70% B in 2.50 minutes, 70% B for 0.70 minutes, 70% to 5% B in 0.1 minutes, then stop | 200 | 0.95 |

-continued

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| H | Shim-pack XR-ODS 2.2 μm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 0.95 |
| I | Shim-pack XR-ODS 2.2 μm 3.0 × 50 mm | Water/0.05% TFA | ACN/0.05% TFA | 1 | 5% to 100% B in 1.20 minutes, 100% B for 1.00 minutes, 100% to 5% B in 0.1 minutes, then stop | 250 | 0.95 |
| J | Shim-pack XR-ODS 2.2 μm 3.0 × 50 mm | Water/0.05% TFA | ACN/0.05% TFA | 1 | 5% to 70% B in 3.20 minutes, 70% B for 0.75 minutes, 70% to 5% B in 0.35 minutes, then stop | 250 | 0.95 |
| K | Shim-pack XR-ODS 2.2 μm 3.0 × 50 mm | Water/0.05% TFA | ACN/0.05% TFA | 1 | 5% to 80% B in 3.00 minutes, 80% B for 0.8 minutes, 80% to 5% B in 0.1 minutes, then stop | 250 | 1.5 |
| L | Shim-pack XR-ODS 2.2 μm 3.0 × 50 mm | Water/0.05% TFA | ACN/0.05% TFA | 1 | 5% to 100% B in 3.00 minutes, 100% B for 0.8 minutes, 100% to 5% B in 0.1 minutes, then stop | 250 | 1.5 |
| M | Shim-pack XR-ODS 2.2 μm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 1.5 |
| N | Shim-pack XR-ODS 2.2 μm 3.0 × 50 mm | Water/0.05% TFA | ACN/0.05% TFA | 1 | 5% to 80% B in 2.20 minutes, 80% B for 1.0 minutes, 80% to 5% B in 0.1 minutes, then stop | 250 | 1.5 |
| O | Zorbax Eclipse Plus C18 4.6 × 100 mm | Water/0.05% TFA | ACN/0.05% TFA | 1 | 5% to 70% B in 8.00 minutes, 70% B for 2.0 minutes, then stop | 250 | 1.5 |
| P | Shim-pack XR-ODS 2.2 μm 3.0 × 50 mm | Water/0.05% TFA | ACN/0.05% TFA | 1 | 5% to 65% B in 3.00 minutes, 65% B for 0.80 minutes, 100% to 5% B in 0.1 minutes, then stop | 250 | 1.5 |
| Q | Shim-pack XR-ODS 2.2 μm 3.0 × 50 mm | Water/0.05% TFA | ACN/0.05% TFA | 1 | 5% to 60% B in 2.50 minutes, 60% B for 0.7 minutes, 60% to 5% B in 0.1 minutes, then stop | 250 | 0.95 |
| R | Shim-pack XR-ODS 2.2 μm 3.0 × 50 mm | Water/0.05% TFA | ACN/0.05% TFA | 1 | 5% to 50% B in 2.50 minutes, 50% B for 0.7 minutes, 50% to 5% B in 0.1 minutes, then stop | 250 | 0.95 |
| S | XBridge C18 3.5 μm 3.0 × 50 mm | Water/0.05% TFA | ACN/0.05% TFA | 1 | 5% to 95% B in 2.20 minutes, 95% B for 1.00 minutes, 95% to 5% B in 0.1 minutes, then stop | 250 | 0.9 |
| T | Shim-pack XR-ODS 1.6 μm 2.0 × 50 mm | Water/0.05% FA | ACN/0.05% FA | 0.7 | 5% to 100% B in 2.0 minutes, 100% B for 1.1 minutes, 100% to 5% B in 0.1 minutes, then stop | 250 | 0.85 |
| U | Shim-pack XR-ODS 2.2 μm 3.0 × 50 mm | Water/0.05% TFA | ACN/0.05% TFA | 1 | 5% to 40% B in 2.50 minutes, 40% B for 0.7 minutes, 40% to 5% B in 0.1 minutes, then stop | 250 | 0.95 |
| V | Shim-pack XR-ODS 2.2 μm 3.0 × 50 mm | Water/0.05% TFA | ACN/0.05% TFA | 1 | 5% to 60% B in 4.20 minutes, 60% B for 1.0 minutes, 60% to 5% B in 0.1 minutes, then stop | 200 | 1.05 |
| W | Shim-pack XR-ODS 2.2 μm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 200 | 0.95 |
| X | Shim-pack XR-ODS 1.6 μm 2.0 × 50 mm | Water/0.05% FA | ACN/0.05% FA | 0.7 | 5% to 100% B in 2.0 minutes, 100% B for 1.1 minutes, 100% to 5% B in 0.1 minutes, then stop | 200 | 0.85 |
| Y | Ecliplis Plus C18 3.5 μm 4.6 × 50 mm | Water/0.05% TFA | ACN | 1 | 5% to 100% B in 2.0 minutes, 100% B for 1.0 minutes, 100% to 5% B in 0.1 minutes, then stop | 250 | 1 |

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| Z | Ecliplis Plus C18 3.5 µm 4.6 × 50 mm | Water/10 mM ammonium carbonate | ACN/5% water | 1 | 5% to 100% B in 2.0 minutes, 100% B for 1.0 minutes, 100% to 5% B in 0.1 minutes, then stop | 250 | 1.1 |
| A1 | Shim-pack XR-ODS 2.2 µm 3.0 × 50 mm | Water/0.05% TFA | ACN | 1 | 5% to 100% B in 2.0 minutes, 100% B for 1.0 minutes, 100% to 5% B in 0.1 minutes, then stop | 250 | 1 |
| A2 | Ecliplis Plus C18 3.5 µm 4.6 × 50 mm | Water/10 mM ammonium acetate | ACN | 1 | 5% to 100% B in 2.0 minutes, 100% B for 1.4 minutes, 100% to 5% B in 0.1 minutes, then stop | 250 | 0.95 |
| A3 | Acquity BEH C18 1.7 µm 2.1 × 50 mm | Water/5 mM ammonium acetate/ 0.1% FA | ACN/0.1% FA | 0.55 | 5% B at 0.01 min up to 0.4 min, 35% B at 0.8 min, 55% B at 1.2 min, 100% B in 1.3 minutes, at 2.5 min up to 3.30 min, 5% B at 3.31 min up to 4.0 min, then stop | | |

Compound structure confirmations were carried out using standard 300 or 400 MHz NMR spectrometers with NOe's conducted whenever necessary.

The following abbreviations are used herein:

| Abbreviation | Meaning |
|---|---|
| ACN | acetonitrile |
| atm. | atmosphere |
| DCM | dichloromethane |
| DHP | dihydropyran |
| DIBAL | diisobutyl aluminum hydride |
| DIEA | diisopropyl ethylamine |
| DMF | dimethyl formamide |
| DMF-DMA | dimethyl formamide dimethyl acetal |
| DMSO | dimethyl sulfoxide |
| dppf | 1,1'-bis(diphenylphosphino)ferrocene |
| EA | ethyl acetate |
| ESI | electrospray ionization |
| EtOH | ethanol |
| FA | formic acid |
| GC | gas chromatography |
| h | hour |
| Hex | hexanes |
| HMDS | hexamethyl disilazide |
| HPLC | high performance liquid chromatography |
| IPA | isopropanol |
| LCMS | liquid chromatography/mass spectrometry |
| MeOH | methanol |
| min | minutes |
| NBS | N-bromo succinimide |
| NCS | N-chloro succinimide |
| NIS | N-iodo succinimide |
| NMR | nuclear magnetic resonance |
| NOe | nuclear Overhauser effect |
| Prep. | preparative |
| PTSA | para-toluene sulfonic acid |
| Rf | retardation factor |
| rt | room temperature |
| RT | retention time |
| sat. | saturated |
| SGC | silica gel chromatography |
| TBAF | tetrabutyl ammonium fluoride |
| TEA | triethylamine |
| TFA | trifluoroacetic acid |
| THF | tetrahydrofuran |
| TLC | thin layer chromatography |
| UPLC | ultra performance liquid chromatography |

INTERMEDIATE SYNTHESIS

Synthesis of intermediate tert-butyl (2-(((3-iodo-1-(tetrahydro-2H-pyran-2-yl)-1H-pyrazol-4-yl)methyl)(methyl)amino)ethyl)carbamate

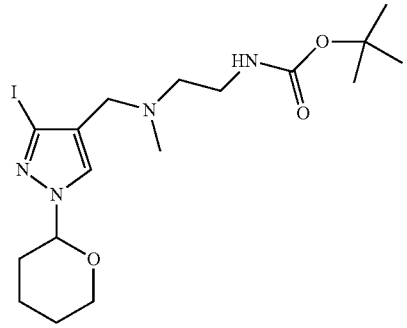 [SMILES: CN(CCNC(=O)OC(C)(C)C)Cc1cn(C2CCCCO2)nc1I]

Step 1: tert-butyl (2-(((3-iodo-1-(tetrahydro-2H-pyran-2-yl)-1H-pyrazol-4-yl)methyl)(methyl)amino)ethyl)carbamate

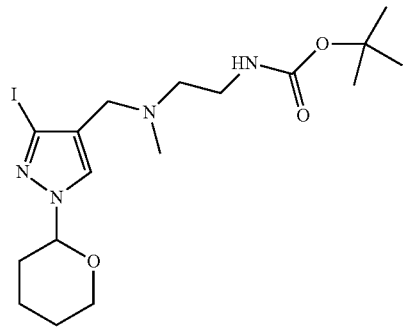 [SMILES: CN(CCNC(=O)OC(C)(C)C)Cc1cn(C2CCCCO2)nc1I]

A mixture of 3-iodo-1-(oxan-2-yl)-1H-pyrazole-4-carbaldehyde (3.2 g, 10.45 mmol, 1.00 equiv), tert-butyl N-[2-

(methylamino)ethyl]carbamate (2.2 g, 12.63 mmol, 1.21 equiv) and NaBH(OAc)₃ (6.65 g, 31.38 mmol, 3.00 equiv) in dichloroethane (30 mL) was stirred for 2 h at room temperature. The reaction was quenched with 50 mL of saturated aqueous sodium bicarbonate solution. The resulting mixture was extracted with 3×200 mL of dichloromethane. The combined organic layers was dried over anhydrous sodium sulfate and concentrated under vacuum. The residue was purified on a silica gel column eluted with 30-100% ethyl acetate in petroleum ether to give 4.05 g (83%) of tert-butyl (2-(((3-iodo-1-(tetrahydro-2H-pyran-2-yl)-1H-pyrazol-4-yl)methyl)(methyl)amino)ethyl)carbamate as a light yellow oil. ¹H NMR (300 MHz, CDCl₃): δ 7.48 (s, 1H), 5.35-5.30 (m, 1H), 4.13-4.03 (m, 1H), 3.71-3.63 (m, 1H), 3.36 (s, 2H), 3.26-3.25 (m, 2H), 2.52-2.49 (m, 2H), 2.21 (s, 3H), 2.09-2.01 (m, 3H), 1.68-1.58 (m, 3H), 1.44 (s, 9H) ppm. LCMS (method C, ESI): RT=0.58 min, m/z=465.0 [M+H]⁺.

Synthesis of intermediate tert-butyl (2-(((3-iodo-1-(tetrahydro-2H-pyran-2-yl)-1H-pyrazol-4-yl)methyl)(methyl)amino)ethyl)(methyl)carbamate

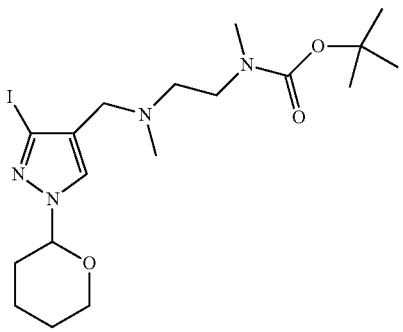 [SMILES: CN(CCN(C)C(=O)OC(C)(C)C)Cc1cn(C2CCCCO2)nc1I]

Step 1: Ethyl 3-iodo-1H-pyrazole-4-carboxylate

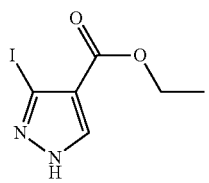

To a stirred solution of ethyl 3-amino-1H-pyrazole-4-carboxylate (10 g, 64.45 mmol, 1.00 equiv) in 50% sulfuric acid (90 mL) at 5° C. was added dropwise a solution of NaNO₂ (7.4 g, 107.25 mmol, 1.66 equiv) in water (15 mL). The reaction was stirred at 5° C. for another 30 min. A solution of KI (32.1 g, 193.37 mmol, 3.00 equiv) in water (15 mL) was added dropwise at 5° C. The reaction was allowed to stir at 5° C. for 1 h and then quenched by the addition of 50 mL of water. The precipitate was collected by filtration and then dissolved in 150 mL of ethyl acetate. The resulting solution was washed sequentially with 1×100 mL of saturated Na₂SO₃ solution, 1×100 mL of saturated sodium bicarbonate solution and 1×100 mL of brine. The organic layer was dried over anhydrous sodium sulfate and concentrated under vacuum to give 10.8 g (63%) of ethyl 3-iodo-1H-pyrazole-4-carboxylate as a yellow solid. ¹H NMR (300 MHz, CDCl₃): δ 8.18 (s, 1H), 4.38-4.29 (m, 2H), 1.41-1.33 (m, 3H) ppm. LCMS (method B, ESI): RT=1.36 min, m/z=267.0 [M+H]⁺.

Step 2: Ethyl 3-iodo-1-(tetrahydro-2H-pyran-2-yl)-1H-pyrazole-4-carboxylate

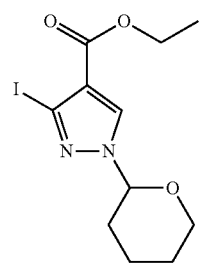 [SMILES: CCOC(=O)c1cn(C2CCCCO2)nc1I]

A solution of ethyl 3-iodo-1H-pyrazole-4-carboxylate (10.8 g, 40.60 mmol, 1.00 equiv), 3,4-dihydro-2H-pyran (10 g, 118.88 mmol, 2.93 equiv) and TsOH (780 mg, 4.53 mmol, 0.11 equiv) in THF (100 mL) was stirred for 2 h at 60° C. The reaction mixture was cooled to room temperature and quenched by the addition of 100 mL of saturated sodium bicarbonate solution. The resulting solution was extracted with 2×80 mL of dichloromethane. The combined organic layers was dried over anhydrous sodium sulfate and concentrated under vacuum. The residue was purified on a silica gel column eluted with ethyl acetate/petroleum ether (1:20) to give 13 g (91%) of ethyl 3-iodo-1-(oxan-2-yl)-1H-pyrazole-4-carboxylate as a yellow oil. ¹H NMR (400 MHz, CDCl₃): δ 8.04 (s, 1H), 5.40-5.38 (m, 1H), 4.34-4.29 (m, 2H), 4.08-4.05 (m, 1H), 3.73-3.70 (m, 1H), 2.07-1.98 (m, 3H), 1.69-1.62 (m, 3H), 1.39-1.32 (m, 3H) ppm. LCMS (method C, ESI): RT=1.53 min, m/z=351.0 [M+H]⁺.

Step 3: 3-Iodo-1-(tetrahydro-2H-pyran-2-yl)-1H-pyrazole-4-carboxylic acid

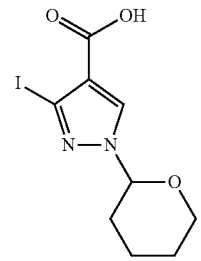 [SMILES: O=C(O)c1cn(C2CCCCO2)nc1I]

To a solution of ethyl 3-iodo-1-(oxan-2-yl)-1H-pyrazole-4-carboxylate (85 g, 242.75 mmol, 1.00 equiv) in THF (300 mL) and methanol (300 mL) was added a solution of LiOH (17.5 g, 730.69 mmol, 3.01 equiv) in water (400 mL). The resulting solution was stirred at room temperature overnight and then concentrated under vacuum to remove the organic solvent. The resulting solution was diluted with 400 mL of H₂O and then acidified to pH 6.0 with 1M hydrochloric acid. The mixture was extracted with 3×800 mL of dichloromethane. The combined organic layers was washed with 3×1000 mL of brine, dried over anhydrous sodium sulfate and concentrated under vacuum to give 75 g (96%) of 3-iodo- 1-(oxan-2-yl)-1H-pyrazole-4-carboxylic acid as an off-white solid. LCMS (method D, ESI): RT=1.23 min, m/z=323.0 [M+H]+.

Step 4: (3-iodo-1-(tetrahydro-2H-pyran-2-yl)-1H-pyrazol-4-yl)methanol

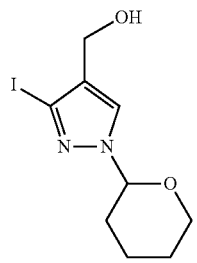 [SMILES: OCc1cn(C2CCCCO2)nc1I]

To a solution of 3-iodo-1-(oxan-2-yl)-1H-pyrazole-4-carboxylic acid (28 g, 86.93 mmol, 1.00 equiv) in anhydrous THF (300 mL) maintained under nitrogen at 5° C. was added a 1M solution of $BH_3$ in THF (300 mL) dropwise with stirring. The reaction was stirred overnight at room temperature and then quenched by the addition of 300 mL of saturated $NH_4Cl$ solution. The resulting mixture was extracted with 3×1000 mL of dichloromethane. The combined organic layers was dried over anhydrous sodium sulfate and concentrated under vacuum. The residue was purified on a silica gel column eluted with ethyl acetate/petroleum ether (1:1) to give 12.67 g (47%) of (3-iodo-1-(oxan-2-yl)-1H-pyrazol-4-yl)methanol as a white solid. $^1$H NMR (400 MHz, DMSO-d6): δ 7.73 (s, 1H), 5.37-5.34 (m, 1H), 4.92 (s, 1H), 4.20 (d, J=3.6 Hz, 2H), 3.89-3.88 (m, 1H), 3.65-3.57 (m, 1H), 2.09-2.00 (m, 1H), 1.99-1.90 (m, 2H), 1.69-1.61 (m, 1H), 1.49-1.46 (m, 2H) ppm. LCMS (method A, ESI): RT=1.16 min, m/z=309.0 [M+H]+.

Step 5: 3-Iodo-1-(tetrahydro-2H-pyran-2-yl)-1H-pyrazole-4-carbaldehyde

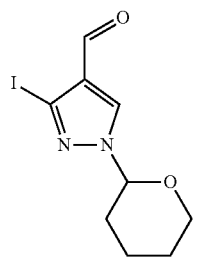 [SMILES: O=Cc1cn(C2CCCCO2)nc1I]

Into a 250-mL 3-necked round-bottom flask purged and. To a stirred solution of oxalyl chloride (18.576 g, 146.35 mmol, 3.01 equiv) in anhydrous dichloromethane (300 mL) maintained under nitrogen at −78° C. was added DMSO (15.138 g, 193.75 mmol, 3.98 equiv) dropwise. The reaction mixture was stirred at −65° C. for 30 min. A solution of (3-iodo-1-(oxan-2-yl)-1H-pyrazol-4-yl)methanol (15.0 g, 48.68 mmol, 1.00 equiv) in dichloromethane (100 mL) was then added dropwise at −65° C. and the reaction was stirred for another 60 min at −65° C. Triethylamine (40.6 mL) was added dropwise at −65° C. and the reaction was stirred for 30 min at −65° C. The reaction was warmed to 0° C. then quenched by the addition of 100 mL of saturated $NH_4Cl$ solution. The resulting mixture was extracted with 3×400 mL of dichloromethane. The combined organic layers was dried over anhydrous sodium sulfate and concentrated under vacuum. The residue was purified on a silica gel column eluted with ethyl acetate/petroleum ether (1:20) to give 13.48 g (90%) of 3-iodo-1-(oxan-2-yl)-1H-pyrazole-4-carbaldehyde as a golden oil. $^1$H NMR (300 MHz, DMSO-d6): δ 9.69 (s, 1H), 8.57 (s, 1H), 5.49 (dd, J=2.7 Hz, 9.9 Hz, 1H), 3.95-3.91 (m, 1H), 3.68-3.62 (m, 1H), 2.11-2.01 (m, 3H), 1.69-1.62 (m, 3H) ppm. LCMS (method A, ESI): RT=1.35 min, m/z=307.0 [M+H]+.

Step 6: tert-Butyl (2-(((3-iodo-1-(tetrahydro-2H-pyran-2-yl)-1H-pyrazol-4-yl)methyl)(methyl)amino) ethyl)(methyl)carbamate

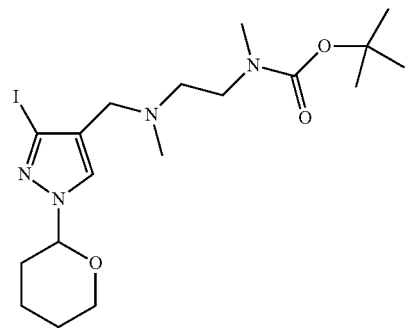 [SMILES: CN(CCN(C)C(=O)OC(C)(C)C)Cc1cn(C2CCCCO2)nc1I]

A mixture of 3-iodo-1-(oxan-2-yl)-1H-pyrazole-4-carbaldehyde (21.5 g, 70.24 mmol, 1.00 equiv), tert-butyl N-methyl-N-(2-(methylamino)ethyl)carbamate (20 g, 106.23 mmol, 1.51 equiv) and NaBH(OAc)$_3$ (29.8 g, 137.98 mmol, 1.96 equiv) in dichloroethane (300 mL) was stirred for 1 h at room temperature. The reaction was diluted with 300 mL of dichloromethane and then washed with 3×300 mL of brine. The organic layer was dried over anhydrous sodium sulfate and concentrated under vacuum. The residue was purified on a silica gel column eluted with 0-7% methanol in dichloromethane to give 31 g (92%) of tert-butyl (2-(((3-iodo-1-(tetrahydro-2H-pyran-2-yl)-1H-pyrazol-4-yl)methyl)(methyl)amino)ethyl)(methyl)carbamate as a yellow oil. $^1$H NMR (300 MHz, CDCl$_3$): δ 7.62 (s, 1H), 5.34-5.30 (m, 1H), 4.06-4.02 (m, 1H), 3.68-3.62 (m, 1H), 3.42-3.38 (m, 4H), 2.85 (s, 4H), 2.62-2.53 (m, 2H), 2.47-2.46 (m, 2H), 2.13-1.97 (m, 3H), 1.74-1.69 (m, 3H), 1.46 (s, 9H) ppm. LCMS (method A, ESI): RT=1.17 min, m/z=479.0 [M+H]+.

Biological Methods

PRMT1 Biochemical Assay

General Materials.

S-adenosylmethionine (SAM), S-adenosylhomocysteine (SAH), bicine, Tween20, dimethylsulfoxide (DMSO), bovine skin gelatin (BSG), and Tris(2-carboxyethyl)phosphine hydrochloride solution (TCEP) are purchased from Sigma-Aldrich at the highest level of purity possible. $^3$H-SAM is purchased from American Radiolabeled Chemicals with a specific activity of 80 Ci/mmol. 384-well streptavidin Flashplates are purchased from PerkinElmer.

Substrates.

Peptide representative of human histone H4 residues 36-50 is synthesized with an N-terminal linker-affinity tag motif and a C-terminal amide cap by 21$^{st}$ Century Biochemicals. The peptide is purified by high-performance liquid chromatography (HPLC) to greater than 95% purity and confirmed by liquid chromatography mass spectrometry (LC-MS). The sequence is Biot-Ahx-RLARRGGVKRIS-GLI-amide (SEQ ID NO.:1).

Molecular Biology:

Full-length human PRMT1 isoform 1 (NM_001536.5) transcript clone is amplified from an HEK 293 cDNA library, incorporating flanking 5' sequence encoding a FLAG tag (DYKDDDDK) (SEQ ID NO.:2) fused directly to Met 1 of PRMT1. The amplified gene is subcloned into pFast-BacI (Life Technologies) modified to encode an N-terminal GST tag and a TEV cleavage sequence (MSPILGYWKIK-GLVQPTRLLLEYLEEKYEEHLYERDEGDKWRNK-KFELGLEFPNLPYYI DGDVKLTQSMAIIRYIADKHN-MLGGCPKERAEISMLEGAVLDIRYGVSRIAYSKDFETLK VDFLSKLPEMLKMFEDRLCHKTYLNGDHVTHPDFM-LYDALDVVLYMDPMCLDAFPKL VCFKKRIEAIPQID-KYLKSSKYIAWPLQGWQATFGGGDHPPKSDENLY-FQGGNS)(SEQ ID NO.:3) fused to Asp of the Flag tag of PRMT1.

Protein Expression.

Recombinant baculovirus are generated according to Bac-to-Bac kit instructions (Life Technologies). Protein over-expression is accomplished by infecting exponentially growing High Five insect cell culture at $1.5 \times 10^6$ cell/ml with 1:100 ratio of virus. Infections are carried out at 27° C. for 48 hours, harvested by centrifugation, and stored at −80° C. for purification.

Protein Purification.

Expressed full-length human GST-tagged PRMT1 protein is purified from cell paste by glutathione sepharose affinity chromatography after equilibration of the resin with 50 mM phosphate buffer, 200 mM NaCl, 5% glycerol, 5 mM β-mercaptoethanol, pH7.8 (Buffer A). GST-tagged PRMT1 is eluted with 50 mM Tris, 2 mM glutathione, pH 7.8, dialysed in buffer A and concentrated to 1 mg/mL. The purity of recovered protein is 73%. Reference: Wasilko, D. J. and S. E. Lee: "TIPS: titerless infected-cells preservation and scale-up" Bioprocess J., 5 (2006), pp. 29-32.

Predicted Translations:

```
GST-tagged PRMT1
                                    (SEQ ID NO.: 4)
MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPKSDENLYFQGGNSDYKDDDDKMAAAEAA

NCIMENFVATLANGMSLQPPLEEVSCGQAESSEKPNAEDMTSKDYYFDS

YAHFGIHEEMLKDEVRTLTYRNSMFHNRHLFKDKVVLDVGSGTGILCMF

AAKAGARKVIGIECSSISDYAVKIVKANKLDHVVTIIKGKVEEVELPVE

KVDIIISEWMGYCLFYESMLNTVLYARDKWLAPDGLIFPDRATLYVTAI

EDRQYKDYKIHWWENVYGFDMSCIKDVAIKEPLVDVVDPKQLVTNACLI

KEVDIYTVKVEDLTFTSPFCLQVKRNDYVHALVAYFNIEFTRCHKRTGF

STSPESPYTHWKQTVFYMEDYLTVKTGEEIFGTIGMRPNAKNNRDLDFT

IDLDFKGQLCELSCSTDYRMR
```

General Procedure for PRMT1 Enzyme Assays on Peptide Substrates.

The assays are all performed in a buffer consisting of 20 mM Bicine (pH=7.6), 1 mM TCEP, 0.005% BSG, and 0.002% Tween 20, prepared on the day of use. Compounds in 100% DMSO (1 ul) are spotted into a polypropylene 384-well V-bottom plates (Greiner) using a Platemate Plus outfitted with a 384-channel head (Thermo Scientific). DMSO (1 ul) is added to Columns 11, 12, 23, 24, rows A-H for the maximum signal control and 1 ul of SAH, a known product and inhibitor of PRMT1, is added to columns 11, 12, 23, 24, rows I-P for the minimum signal control. A cocktail (40 ul) containing the PRMT1 enzyme is added by Multi-drop Combi (Thermo-Fisher). The compounds are allowed to incubate with PRMT1 for 30 min at room temperature, then a cocktail (10 ul) containing SAM and peptide is added to initiate the reaction (final volume=51 ul). The final concentrations of the components are as follows: PRMT1 is 0.5 nM, $^3$H-SAM is 200 nM, non-radiolabeled SAM is 1.5 uM, peptide is 20 nM, SAH in the minimum signal control wells is 1 mM, and the DMSO concentration is 2%. The assays are stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate are then transferred to a 384-well Flashplate and the biotinylated peptides are allowed to bind to the streptavidin surface for at least 1 hour before being washed once with 0.1% Tween20 in a Biotek ELx405 plate washer. The plates are then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \text{ inh} = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC$_{50}$ Fit $$Y = \text{Bottom} + \frac{(\text{Top} - \text{Bottom})}{\left(1 + \left(\frac{X}{IC_{50}}\right)^{\text{Hill Coefficient}}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

RKO Methylation Assay

RKO adherent cells are purchased from ATCC (American Type Culture Collection), Manassas, Va., USA. DMEM/Glutamax medium, penicillin-streptomycin, heat inactivated fetal bovine serum, 0.05% trypsin and D-PBS are purchased from Life Technologies, Grand Island, N.Y., USA. Odyssey blocking buffer, 800CW goat anti-rabbit IgG (H+L) antibody, and Licor Odyssey infrared scanner are purchased from Licor Biosciences, Lincoln, Nebr., USA. Mono-methyl arginine antibody is purchased from Cell Signaling Technology, Danvers, Mass., USA. Methanol was purchased from VWR, Franklin, Mass., USA. 10% Tween 20 is purchased from KPL, Inc., Gaithersburg, Md., USA. DRAQ5 is purchased from Biostatus Limited, Leicestershire, UK.

RKO adherent cells are maintained in growth medium (DMEM/Glutamax medium supplemented with 10% v/v heat inactivated fetal bovine serum and 100 units/mL penicillin-streptomycin) and cultured at 37° C. under 5% $CO_2$.

Cell Treatment, in Cell Western (ICW) for Detection of Mono-Methyl Arginine and DNA Content.

RKO cells are seeded in assay medium at a concentration of 20,000 cells per mL to a poly-D-lysine coated 384 well culture plate (BD Biosciences 356697) with 50 µL per well. Compound (100 nL) from a 96-well source plate is added directly to 384 well cell plate. Plates are incubated at 37° C., 5% $CO_2$ for 72 hours. After three days of incubation, plates are brought to room temperature outside of the incubator for ten minutes and blotted on paper towels to remove cell media. 50 µL of ice cold 100% methanol are added directly to each well and incubated for 30 min at room temperature. After 30 min, plates are transferred to a Biotek EL406 plate washer and washed 2 times with 100 µL per well of wash buffer (1×PBS). Next 60 µL per well of Odyssey blocking buffer (Odyssey Buffer with 0.1% Tween 20 (v/v)) are added to each plate and incubated 1 hour at room temperature. Blocking buffer is removed and 20 µL per well of primary antibody is added (mono-methyl arginine diluted 1:200 in Odyssey buffer with 0.1% Tween 20 (v/v)) and plates are incubated overnight (16 hours) at 4° C. Plates are washed 5 times with 100 µL per well of wash buffer. Next 20 µL per well of secondary antibody are added (1:200 800CW goat anti-rabbit IgG (H+L) antibody, 1:1000 DRAQ5 (Biostatus limited) in Odyssey buffer with 0.1% Tween 20 (v/v)) and incubated for 1 hour at room temperature. The plates are washed 5 times with 100 µL per well wash buffer then 2 times with 100 µL per well of water. Plates are allowed to dry at room temperature then imaged on the Licor Odyssey machine which measures integrated intensity at 700 nm and 800 nm wavelengths. Both 700 and 800 channels are scanned.

Calculations:

First, the ratio for each well is determined by:

$$\left(\frac{\text{monomethyl Arginine 800 nm value}}{DRAQ5\ 700\ \text{nm value}}\right)$$

Each plate includes fourteen control wells of DMSO only treatment (minimum activation) as well as fourteen control wells for maximum activation that is treated with 20 µM of a reference compound. The average of the ratio values for each control type is calculated and used to determine the percent activation for each test well in the plate. Reference compound is serially diluted three-fold in DMSO for a total of nine test concentrations, beginning at 20 µM. Percent activation is determined and $EC_{30}$ curves are generated using triplicate wells per concentration of compound.

Percent Activation =

$$100 - \left(\left(\frac{(\text{Individual Test Sample Ratio}) - (\text{Minimum Activation Ratio})}{(\text{Maximum Activation Ratio}) - (\text{Minimum Activation Ratio})}\right) * 100\right)$$

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of therapeutic treatment of a PRMT1-mediated disorder, comprising administering to a subject in need thereof a therapeutically effective amount of a compound of Formula (I-a) or (I-b):

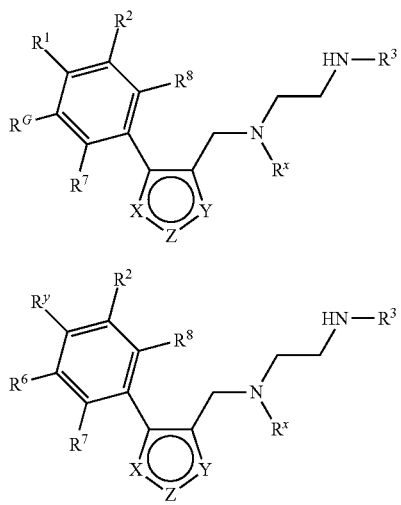

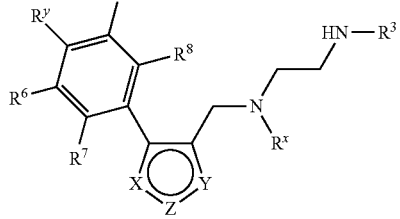

or a pharmaceutically acceptable salt thereof,
wherein
X is N, Z is $NR^4$, and Y is $CR^5$; or
X is $NR^4$, Z is N, and Y is $CR^5$; or
X is $CR^5$, Z is $NR^4$, and Y is N; or
X is $CR^5$, Z is N, and Y is $NR^4$;
$R^G$ is $CF_3$ or $CF_2H$;
$R^1$ is hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$(CR^ZR^Z)_nC(O)N(R^B)_2$, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(O)R^A$, —$OS(O)_2R^A$, —$SO_2R^A$, —$NR^BSO_2R^A$, or —$SO_2N(R^B)_2$;

$R^2$ is hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(O)R^A$, —$OS(O)_2R^A$, —$SO_2R^A$, —$NR^BSO_2R^A$, or —$SO_2N(R^B)_2$;

$R^6$ is hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(O)R^A$, —$OS(O)_2R^A$, —$SO_2R^A$, —$NR^BSO_2R^A$, or —$SO_2N(R^B)_2$;

$R^7$ and $R^8$ are independently selected from the group consisting of hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, and —SO$_2$N(R$^B$)$_2$; wherein at least one of R$^7$ and R$^8$ is not hydrogen;

each R$^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

each R$^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, and a nitrogen protecting group, or two R$^B$ groups are taken together with their intervening atoms to form an optionally substituted heterocyclic ring;

R$^1$ and R$^2$ are optionally taken together to form a carbocyclic, heterocyclic, or aryl ring; or R$^2$ and R$^8$ are optionally taken together to form a carbocyclic, heterocyclic, or aryl ring; or R$^6$ and R$^7$ are optionally taken together to form a carbocyclic, heterocyclic, or aryl ring;

R$^3$ is hydrogen, C$_{1-4}$ alkyl, or C$_{3-4}$ cycloalkyl;

R$^4$ is hydrogen, optionally substituted C$_{1-6}$ alkyl, optionally substituted C$_{2-6}$ alkenyl, optionally substituted C$_{2-6}$ alkynyl, optionally substituted C$_{3-7}$ cycloalkyl, optionally substituted 4- to 7-membered heterocyclyl, or optionally substituted C$_{1-4}$ alkyl-Cy;

Cy is optionally substituted C$_{3-7}$ cycloalkyl, optionally substituted 4- to 7-membered heterocyclyl, optionally substituted aryl, or optionally substituted heteroaryl;

R$^5$ is hydrogen, halo, —CN, optionally substituted C$_{1-4}$ alkyl, or optionally substituted C$_{3-4}$ cycloalkyl;

R$^x$ is optionally substituted C$_{1-4}$ alkyl or optionally substituted C$_{3-4}$ cycloalkyl;

R$^y$ is —NR$^B$C(O)R$^A$, —NR$^B$SO$_2$R$^A$, or —(CR$^z$R$^z$)$_n$C(O)N(R$^B$)$_2$;

each R$^z$ is independently hydrogen or fluoro; and n is 0, 1, 2, 3, or 4;

wherein the PRMT1-mediated disorder is selected from breast cancer, prostate cancer, lung cancer, colon cancer, bladder cancer, leukemia, lymphoma, diabetes mellitus, kidney failure, coronary heart disease, oculopharyngeal muscular dystrophy, and amyotrophic lateral sclerosis.

2. The method of claim 1 wherein R$^1$ is hydrogen, —OR$^A$, —CN, halo, optionally substituted alkyl, optionally substituted alkenyl, optionally substituted alkynyl, or optionally substituted carbocyclic.

3. The method of claim 1, wherein R$^2$ is hydrogen, —OR$^A$, —CN, halo, optionally substituted alkyl, optionally substituted alkenyl, optionally substituted alkynyl, or optionally substituted carbocyclic.

4. The method of claim 1, wherein R$^7$ is hydrogen and R$^8$ is not hydrogen or wherein R$^7$ is not hydrogen and R$^8$ is hydrogen.

5. The method of claim 1, wherein R$^3$ is hydrogen, methyl, ethyl, propyl, butyl, cyclopropyl, or cyclobutyl.

6. The method of claim 1, wherein R$^4$ is hydrogen or optionally substituted C$_{1-6}$ alkyl.

7. The method of claim 1, wherein R$^5$ is hydrogen or optionally substituted C$_{1-4}$ alkyl.

8. The method of claim 1, wherein R$^x$ is methyl, ethyl, propyl, butyl, isopropyl, hydroxyethyl, methoxyethyl, cyclopropyl, or cyclobutyl.

9. The method of claim 1, wherein the compound is selected from the group consisting of:

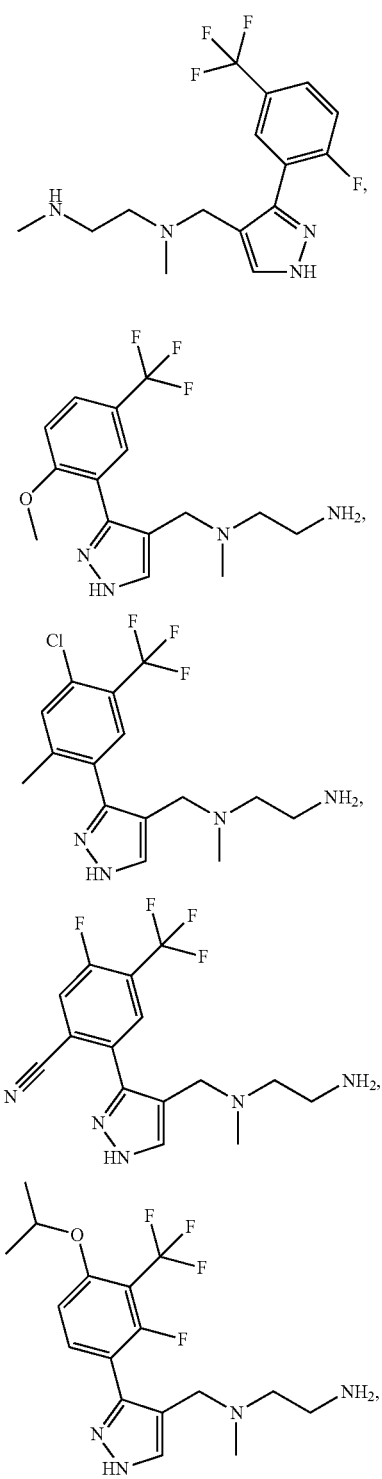

-continued
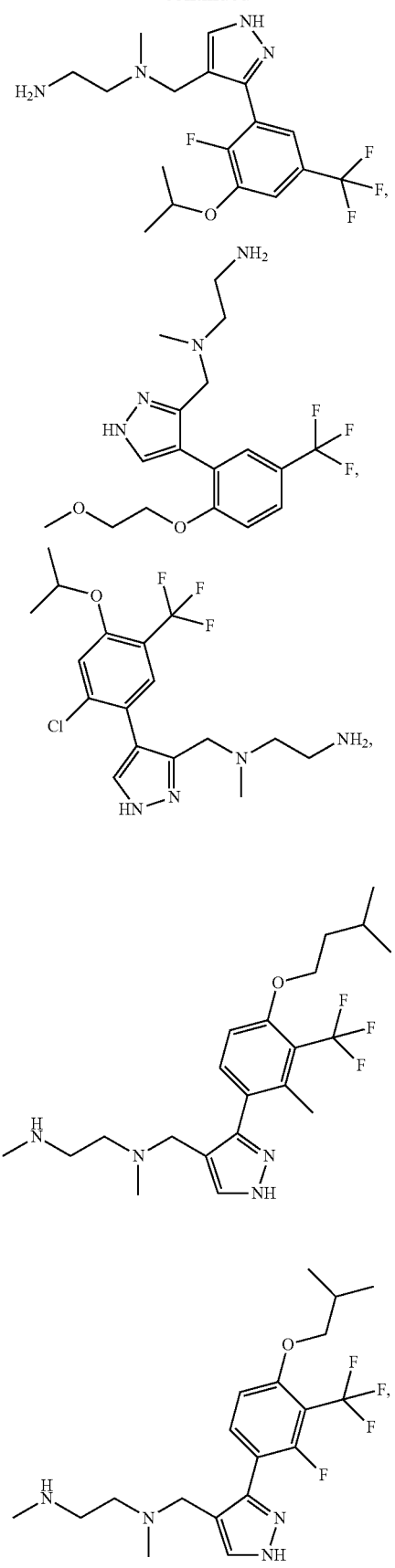
-continued
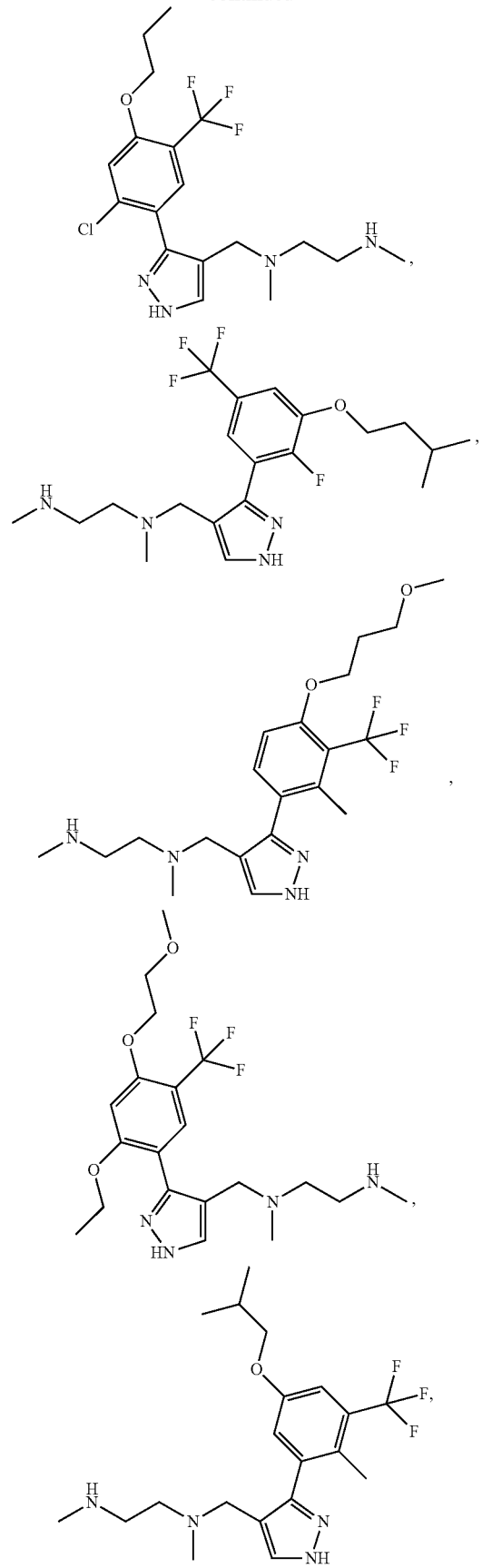

101
-continued
102
-continued
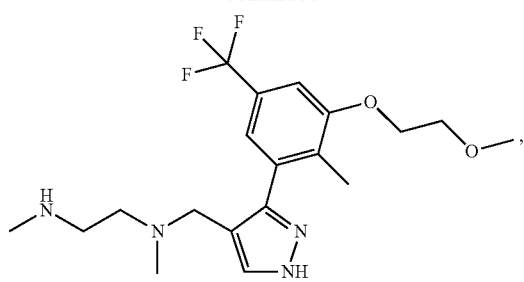
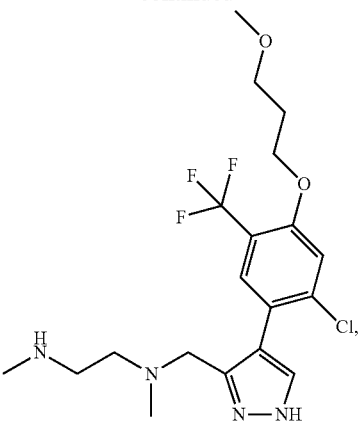
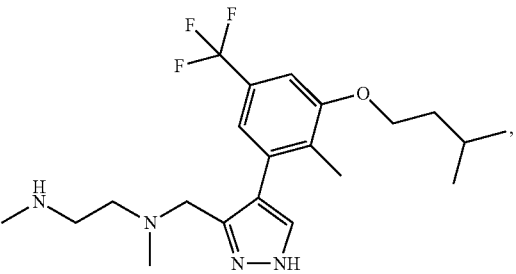
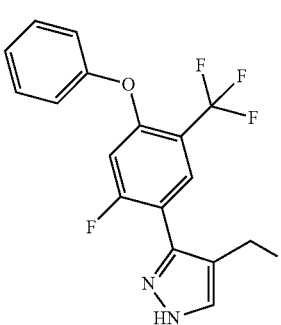

103
-continued
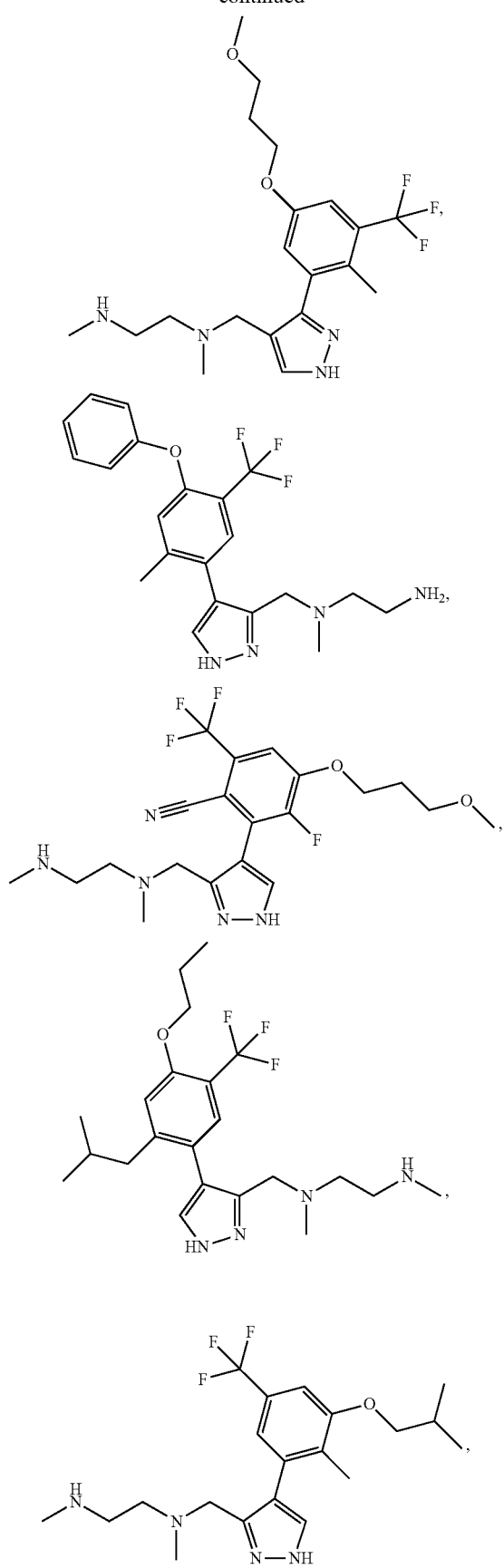
104
-continued
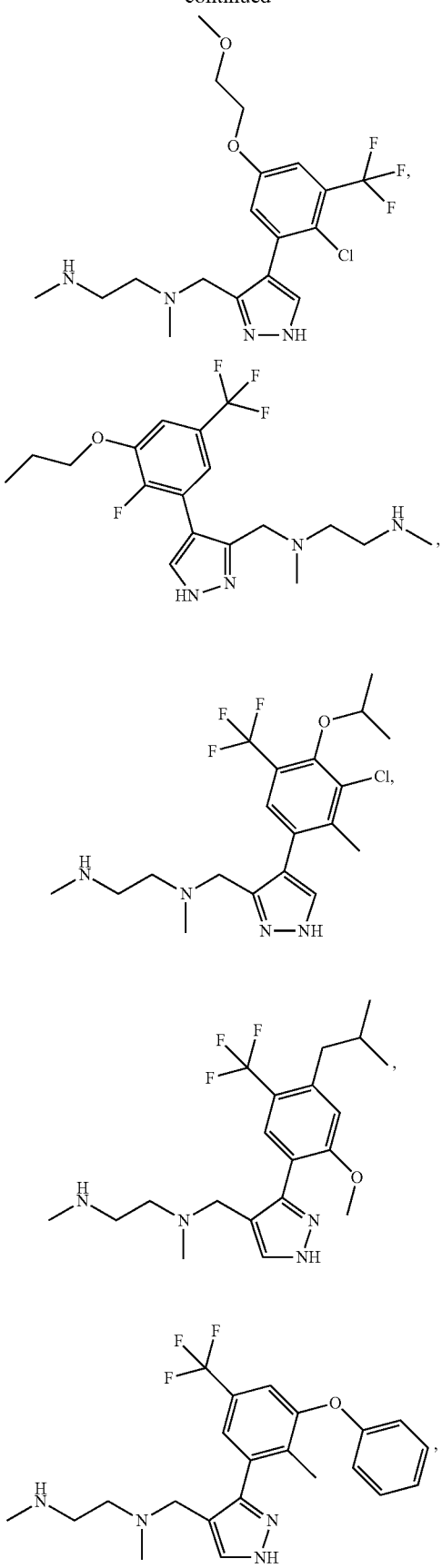

-continued

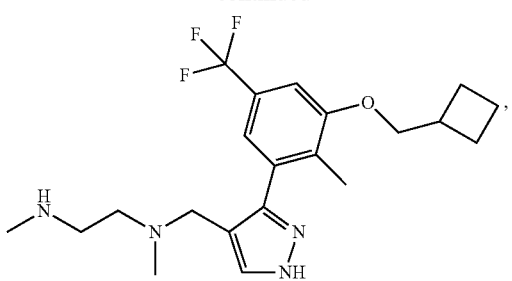

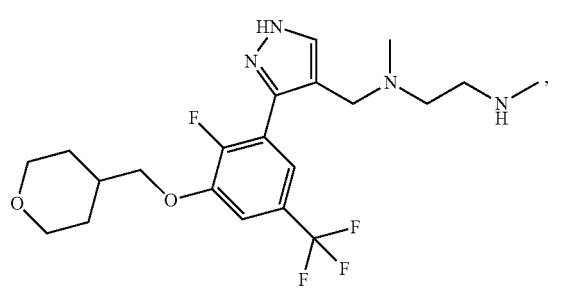

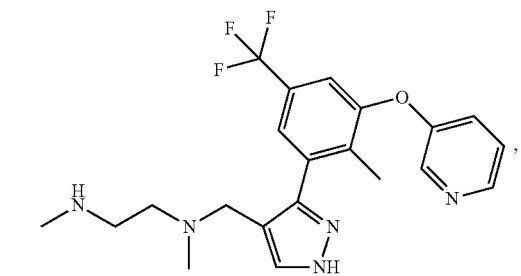

-continued

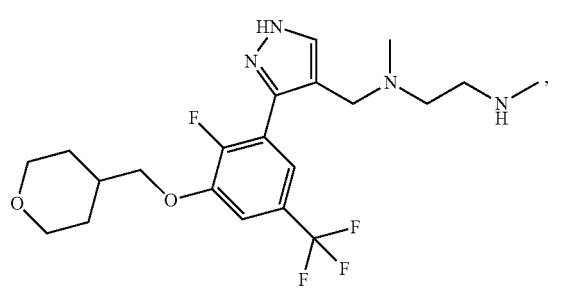

and pharmaceutically acceptable salts thereof.

10. The method of claim 1, wherein the PRMT1-mediated disorder is selected from breast cancer, prostate cancer, lung cancer, colon cancer, bladder cancer, leukemia, and lymphoma.

11. The method of claim 10, wherein the PRMT1-mediated disorder is leukemia.

12. The method of claim 10, wherein the PRMT1-mediated disorder is lymphoma.

13. The method of claim 1, wherein the PRMT1-mediated disorder is selected from diabetes mellitus, kidney failure, coronary heart disease, oculopharyngeal muscular dystrophy, and amyotrophic lateral sclerosis.

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Arg Leu Ala Arg Arg Gly Gly Val Lys Arg Ile Ser Gly Leu Ile
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

Asp Tyr Lys Asp Asp Asp Asp Lys
1               5
```

```
<210> SEQ ID NO 3
<211> LENGTH: 230
<212> TYPE: PRT
<213> ORGANISM: Artificial Sequence
<220> FEATURE:
<223> OTHER INFORMATION: Synthetic Polypeptide

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Glu Asn Leu Tyr
    210                 215                 220

Phe Gln Gly Gly Asn Ser
225                 230

<210> SEQ ID NO 4
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

-continued

```
                65                  70                  75                  80
        Met Leu Gly Gly Cys Pro Lys Glu Arg Ala Glu Ile Ser Met Leu Glu
                            85                  90                  95

Gly Ala Val Leu Asp Ile Arg Tyr Gly Val Ser Arg Ile Ala Tyr Ser
                            100                 105                 110

Lys Asp Phe Glu Thr Leu Lys Val Asp Phe Leu Ser Lys Leu Pro Glu
                            115                 120                 125

Met Leu Lys Met Phe Glu Asp Arg Leu Cys His Lys Thr Tyr Leu Asn
                            130                 135                 140

Gly Asp His Val Thr His Pro Asp Phe Met Leu Tyr Asp Ala Leu Asp
        145                 150                 155                 160

Val Val Leu Tyr Met Asp Pro Met Cys Leu Asp Ala Phe Pro Lys Leu
                            165                 170                 175

Val Cys Phe Lys Lys Arg Ile Glu Ala Ile Pro Gln Ile Asp Lys Tyr
                            180                 185                 190

Leu Lys Ser Ser Lys Tyr Ile Ala Trp Pro Leu Gln Gly Trp Gln Ala
                            195                 200                 205

Thr Phe Gly Gly Gly Asp His Pro Pro Lys Ser Asp Glu Asn Leu Tyr
                            210                 215                 220

Phe Gln Gly Gly Asn Ser Asp Tyr Lys Asp Asp Asp Lys Met Ala
        225                 230                 235                 240

Ala Ala Glu Ala Ala Asn Cys Ile Met Glu Asn Phe Val Ala Thr Leu
                            245                 250                 255

Ala Asn Gly Met Ser Leu Gln Pro Pro Leu Glu Glu Val Ser Cys Gly
                            260                 265                 270

Gln Ala Glu Ser Ser Glu Lys Pro Asn Ala Glu Asp Met Thr Ser Lys
                            275                 280                 285

Asp Tyr Tyr Phe Asp Ser Tyr Ala His Phe Gly Ile His Glu Glu Met
                            290                 295                 300

Leu Lys Asp Glu Val Arg Thr Leu Thr Tyr Arg Asn Ser Met Phe His
        305                 310                 315                 320

Asn Arg His Leu Phe Lys Asp Lys Val Val Leu Asp Val Gly Ser Gly
                            325                 330                 335

Thr Gly Ile Leu Cys Met Phe Ala Ala Lys Ala Gly Ala Arg Lys Val
                            340                 345                 350

Ile Gly Ile Glu Cys Ser Ser Ile Ser Asp Tyr Ala Val Lys Ile Val
                            355                 360                 365

Lys Ala Asn Lys Leu Asp His Val Val Thr Ile Ile Lys Gly Lys Val
        370                 375                 380

Glu Glu Val Glu Leu Pro Val Glu Lys Val Asp Ile Ile Ser Glu
        385                 390                 395                 400

Trp Met Gly Tyr Cys Leu Phe Tyr Glu Ser Met Leu Asn Thr Val Leu
                            405                 410                 415

Tyr Ala Arg Asp Lys Trp Leu Ala Pro Asp Gly Leu Ile Phe Pro Asp
                            420                 425                 430

Arg Ala Thr Leu Tyr Val Thr Ala Ile Glu Asp Arg Gln Tyr Lys Asp
                            435                 440                 445

Tyr Lys Ile His Trp Trp Glu Asn Val Tyr Gly Phe Asp Met Ser Cys
                            450                 455                 460

Ile Lys Asp Val Ala Ile Lys Glu Pro Leu Val Asp Val Val Asp Pro
        465                 470                 475                 480

Lys Gln Leu Val Thr Asn Ala Cys Leu Ile Lys Glu Val Asp Ile Tyr
                            485                 490                 495
```

```
Thr Val Lys Val Glu Asp Leu Thr Phe Thr Ser Pro Phe Cys Leu Gln
        500                 505                 510

Val Lys Arg Asn Asp Tyr Val His Ala Leu Val Ala Tyr Phe Asn Ile
        515                 520                 525

Glu Phe Thr Arg Cys His Lys Arg Thr Gly Phe Ser Thr Ser Pro Glu
        530                 535                 540

Ser Pro Tyr Thr His Trp Lys Gln Thr Val Phe Tyr Met Glu Asp Tyr
545                 550                 555                 560

Leu Thr Val Lys Thr Gly Glu Glu Ile Phe Gly Thr Ile Gly Met Arg
                565                 570                 575

Pro Asn Ala Lys Asn Asn Arg Asp Leu Asp Phe Thr Ile Asp Leu Asp
            580                 585                 590

Phe Lys Gly Gln Leu Cys Glu Leu Ser Cys Ser Thr Asp Tyr Arg Met
        595                 600                 605

Arg
```